United States Patent [19]

Gefter et al.

[11] Patent Number: 5,019,384
[45] Date of Patent: May 28, 1991

[54] IMMUNONODULATING COMPOSITIONS AND THEIR USE

[75] Inventors: Malcolm L. Gefter, Weston, Mass.; Jean G. Guillet, Paris, France

[73] Assignee: Massachusetts Institute of Technology, Cambridge, Mass.

[21] Appl. No.: 434,548

[22] Filed: Nov. 13, 1989

Related U.S. Application Data

[63] Continuation of Ser. No. 66,812, Jun. 25, 1987, abandoned, which is a continuation-in-part of Ser. No. 17,343, Feb. 20, 1987, abandoned, which is a continuation-in-part of Ser. No. 924,286, Oct. 29, 1986, abandoned, and a continuation-in-part of Ser. No. 880,134, Jun. 30, 1986, abandoned.

[51] Int. Cl.[5] .................. A61K 39/00; A61K 39/002; A61K 39/02; A61K 39/12
[52] U.S. Cl. ..................................... 424/88; 424/89; 424/92
[58] Field of Search ........................... 424/88, 89, 92

[56] References Cited

U.S. PATENT DOCUMENTS

| | | | |
|---|---|---|---|
| 4,285,930 | 8/1981 | Likhite | 424/88 |
| 4,469,677 | 9/1984 | Michael et al. | 424/91 |
| 4,473,555 | 9/1984 | Nestor et al. | 424/177 |
| 4,478,823 | 10/1984 | Sanderson | 424/88 |
| 4,565,696 | 1/1986 | Heath et al. | 424/88 |
| 4,599,230 | 7/1986 | Milich et al. | 424/89 |
| 4,683,136 | 7/1987 | Milich et al. | 530/403 |
| 4,707,357 | 11/1987 | Dame et al. | 424/88 |
| 4,722,840 | 2/1988 | Valenzuela et al. | 530/350 |

OTHER PUBLICATIONS

T-Lymphocyte Recognition of Antigen in Association with Gene Products of the Major Histocompatability Complex, Schwartz, Ann. Rev. Immunol. (1985) 3:237–261.
Structural Feature of Protein Antigenic Sites Recognized by Helper T Cells: What Makes a Site Immunodominant, Berzofsky, The Year in Immunology (1986) 2: 28–38.
Ia Molecule-Associated Selectivity in T Cell Recognition of a 23 Amino Acid Peptide of Lysozyme, Shastri et al., J Exp. Med. (1986) 164:882–896.
Distinct Recognition Phenotypes Exist for T-Cell Clones Specific for Small Peptide Regions of Proteins, Shastri et al., J. Exp. Med. (1985) 162:332–345.
The Basis for the Immunoregulatory Role of Macrophages and Other Accessory Cells, Unanue and Allen, Science, (1987) 236:551–557.
Interaction of Peptide Antigens and Class II Major Histocompatability Complex Antigen, Guillet et al., Nature (1986) 324:260–262.
T-Cell Antigenic Sites Tend To Be Amphipathic Structures, DeLisi and Berzofsky, Proc. Natl. Acad. Sci. USA (1985) 82:7048–7052.
The Epitopes of Influenza Nucleoprotein Recognized by Cytotoxic T-Lymphocytes Can Be Defined With Short, Synthetic Peptides, Townsend et al., Cell (1986) 44:959–968.
T-Cell Activation by Peptide Antigen: Effect of Peptide Sequence and Method of Antigen Presentation, (List continued on next page.)

*Primary Examiner*—John Doll
*Assistant Examiner*—Christina Chan
*Attorney, Agent, or Firm*—Bertram I. Rowland

[57] ABSTRACT

Novel methods or compositions are provided for modulating the immune system, so as to be able to selectively stimulate or inactivate lymphocytes in relation to a particular transplantation antigen content. Particularly, mixtures may be employed associated with the more common transplanatation antigens of a host population. In this manner, a large number of people can be treated, for example, by immunization, stimulation of particular T-cells or B-cells in relation to a pathogenic invasion of other aberrant state, e.g. neoplasia, treatment of autoimmune diseases, and the like. Particularly, the compositions may involve an oligopeptide involving as a first region a consensus sequence and an epitope or the first region may be joined to a second region comprising an antibody target sequence which is capable of competing with an epitopic site of an antigen of interest.

13 Claims, 12 Drawing Sheets

OTHER PUBLICATIONS

Watts et al., Proc. Natl. Acad. Sci. USA (1985) 82:5480–5484.

The T Lymphocyte Response to Cytochrome C, Schwartz et al., J. Immun. (1985) 135:2598–2608.

Binding of Immunogenic Peptides to Ia Histocompatability Molecules, Babbitt et al., Nature (1985) 317:359–361.

Neonatal T–Cell Tolerance to Minimal Immunogenic Peptides is Caused by Clonal Inactivation, Gammon et al., Nature (1986) 319:413–415.

Antigenic Competition at the Level of Peptide–Ia Binding, Babbitt et al., Proc. Natl. Acad. Sci. USA (1986) 83:4509–4513.

T–Cell Mediated Association of Peptide Antigen and Major Histocompatability Complex Protein Detected by Energy Transfer in an Evanescent Wave-Field, Watts et al., Nature (1986) 320:179–181.

T–Cell Repertoire for Recognition of a Phylogenetically Distinct Protein Antigen, Finnegan et al., J. Exp. Med. (1986) 164:897–910.

I–A–Restricted T–Cell Antigen Recognition, Lechler et al., J. Exp. Med. (1986) 163:678–696.

T–Cell Recognition of Antigen and the Ia Molecule as a Ternary Complex, Ashwell and Schwartz, Nature (1986) 320:176–179.

Antigen Recognition by H–2–Restricted T–Cells, Shimonkevitz et al., J. Immunol. (1984) 133:2067–2074.

Molecular Mapping of a Histocompatability-Restricted Immunodominant T–Cell Epitope with Synthetic and Natural Peptides: Implications for T–Cell Antigenic Structure, Berkower et al., J. Immunol. (1986) 136:2498–2503.

Chemically Related Antigens Compete for Presentation by Accessory Cells to T–Cells, Werdelin, J. Immunol. (1982) 129:1883–1891.

Inhibition of Antigen Specific T Lympocyte Activation by Structurally Related Ir Gene-Controlled Polymer, Rock and Benacerraf, J. Exp. Med. (1983) 157:1618–1634.

Inhibition of Antigen Specific T Lympocyte Activation by Structurally Related Ir Gene-Controlled Polymer, Rock and Benacerraf, J. Exp. Med. (1984) 160:1864–1879.

Analogs that Compete for Antigen Binding to an Arsonate-Reactive T–Cell Clone Inhibit the Functional Response to Arsonate, Rao et al., Cell (1984) 36:889–895.

Identification of Distinct Predominant Epitopes Recognized by Myoglobin-Specific T–Cells under the Control of Different Ir Genes and Characterization of Representative T–Cell Clones, Berkower et al., J. Immunol. (1984) 132:1370–1378.

High Frequency and Non-random Distribution of Alloreactivity in T–Cell Clones Selected for Recognition of Foreign Antigen in Association with Self Class II Molecules, Ashwell et al., J. Immunol. (1986) 136:389–395.

Isolation and Characterization of a cDNA Clone with a Murine I-E$_\beta$ Polypeptide Chain, Mengle-Gaw and McDevitt, Proc. Natl. Acad. Sci. USA (1983) 80:7621–7625.

Murine I-A$_\beta$ Chain Polymorphism: Nucleotide Sequences of Three Allelic I-A$_\beta$ Genes, Choi et al., Science (1983) 222:283–286.

Peptides Related to the Antigenic Determinant Block T–Cell Recognition of the Native Protein as Processed by Antigen Presenting Cells, Lakey et al., Eur. J. Immunol. (1986) 16:721–727.

Histocompatability Restrictions Explained, Marx, Science (1987) 235:843–844.

Amphiphilic Secondary Structure: Design of Peptide Hormones, Kaiser and Kezdy, Science (1984) 223:249–254.

Efficacy of Murine Malaria Sporozoite Vaccine: Implications for Human Vaccine Development, Egan et al., Science (1987) 236:453–456.

A Synthetic Decapeptide of Influenza Virus Hemagglutinin Elicits Helper T–Cells with the Same Fine Recognition Specificities as Occur in Response to Whole Virus, Hackett et al., J. Immunol. (1985) 135:1391–1394.

The Somatic Generation of Immune Recognition, Jerne, Eur. J. Immunol. (1971) 1:1–9.

Solids Phase Peptides Synthesis, I, The Synthesis of a Tetrapeptide, Merrifield, J. Am. Chem. Soc. (1963) 85:2149–2154.

Non-overlapping T and B Cell Determinants on a Hepatitis B Surface Antigen Pre-S(2) Lesion Synthesis (List continued on next page.)

OTHER PUBLICATIONS

Peptide, Milich et al., J. Exp. Med. (1986) 164:532–547.
Primary Structure of λ Repressor, Sauer and Anderegg, Biochemistry (1978) 17:1092–1100.
Identification of the Determinant Recognized by Two T-Cell Hybridomas, Allen et al., Proc. Natl. Acad. Sci. USA (1984) 81:2489–2493.
Use of Synthetic Peptides of Influenza Nucleoprotein to Define Epitopes Recongized by Class I Restricted Cytotoxic T Lymphocytes, Bastin et al., J. Exp. Med. (1987) 165:1508–1523.
A Possible Immunodominant Epitope Recognized by Murine T Lymphocytes Immune to Different Myoglobins, Berkower et al., Proc. Natl. Acad. Sci. USA (1982) 79:4723–4727.
The Relation between Major Histocompatability Complex (MHC) Restriction in the Capacity of Ia to Bind Immunogenic Peptides, Buus et al., Science (1987) 235:1353–1358.
The Ia Molecule of the Antigen-presenting Cell plays a Critical Role in Immune Response Gene Regulation of T-Cell Activation, Heber-Katz-et al., J. Mol. Cell. Immunol. (1983) 1:3–14.
Absence of Ir Gene of T-Cells Recognizing a Foreign Antigen in the Context of Allogeneic MHC Molecules, Ishii et al., Nature (1982) 295:531–533.
HLA-DQ is Epistatic to HLA-DR in Controlling the Immune Response to Schistosomal Antigen in Humans, Hirayama et al., Nature, (1987) 327:426–430.
Inhibition of Alloreactive Cytotoxic T Lymphocytes by Peptides from the $\alpha_a$ Domain of HLA-A2, Parnham et al., Nature (1987) 235;14 625–628.
Construction of Synthetic Immunogen: Use of New T-Helper Epitope on Malaria Circumsporozoite Protein, Good et al., Science (1987) 235:1059–1062.
Allele-Specific Control of Ia Molecule Surface Expression and Confirmation: Implications for a General Model of Ia Structure-function Relationships, Braunstein and Germain, Proc. Natl. Acad. Sci. USA, (1987) 84:2921–2925.
Guillet et al., Chem. Abstr., vol. 106, No. 154389c (1987).
Sette et al., The Journal of Immunology, vol. 143, No. 10, pp. 3289–3294 (1989).
Rothbard et al., International Immunology, vol. 1, No. 4, pp. 487–495 (1989).
Rothbard et al., International Immunology, vol. 1, No. 5, pp. 479–486 (1989)
Ria et al., Nature, vol. 343, pp. 381–383, (1/25/90).
Adorini et al., Nature, vol. 334, pp. 623–625, (8/18/88).
Anderson et al., Science, vol. 242, pp. 259–261, (1988).
Francis et al., Nature, vol. 330 (12) pp. 168–170, (11/87).
Sette et al., The Journal of Immunology, vol. 142 (1), pp. 35–40 (1989).
Rothbard et al., Cell, vol. 52, pp. 515–523, (1988).
Bodmer et al., Cell, vol. 52, pp. 253–258 (1988).
Rudinger, Peptide Hormones, Parsons (ed.), U Park Press, Baltimore, (1976).
Fauci, PNAS, vol. 83, pp. 9278–9283, (12/86).

|   | 1 | 2 | 3 | 4 | 5 | 6 | 7 | 8 | 9 | 10 | 11 | 12 | 13 | SOURCE |
|---|---|---|---|---|---|---|---|---|---|---|---|---|---|---|
|   | Leu | Glu | Leu | Phe | Arg | Lys | Asp | Ile | Ala | Ala | Lys | Tyr | Lys | Myoglobin (34) |
|   | Val | Glu | Asn | Ala | Lys | Lys | Ile | Glu | Val | Glu | Phe | Asp | Lys | Nuclease (2) |
|   | Leu | Glu | Asp | Ala | Arg | Arg | Leu | Lys | Ala | Ile | Tyr | Glu | Lys | λ Repressor cI (9) |
|   | Leu | Glu | Asp | Ala | Arg | Ala | Ser | Val | Asp | Thr | Tyr | Cys | Arg | I-E$_\beta^d$ (20) |
|   | Leu | Glu | Gln | Lys | Arg | Ala | Glu | Val | Asp | Thr | Val | Cys | Arg | I-E$_\beta^k$ (20) |
| (Leu) | Glu | Arg | Phe | Glu | Ile | Phe | Pro | Lys | Glu |   |   |   |   | Influenza (11) |
|   | Leu | Glu | Arg | Phe |   | Ile | Tyr | Asn | Arg | Glu |   |   |   | I-E$_\beta^d$ (20) |
|   | Leu | Val | Arg | Tyr |   | Phe | Tyr | Asn | Leu | Glu |   |   |   | I-E$_\beta^k$ (20) |

FIG. 5

| | 1 | 2 | 3 | 4 | 5 | 6 | 7 | 8 | 9 | 10 | 11 | 12 | 13 | 14 | 15 | 16 | 17 | 18 | 19 | 20 | SOURCE |
|---|---|---|---|---|---|---|---|---|---|---|---|---|---|---|---|---|---|---|---|---|---|
| | | | | | | | Ala | Val | His | Ala | Ala | His | Ala | Glu | Ile | Asn | Glu | Ala | Gly | Arg | Ovalbumin (10) |
| | Glu | Tyr | Val | Arg | Tyr | Asp | Ser | Asp | Val | Gly | Glu | His | Arg | Ala | Val | Thr | Glu | Leu | Gly | Arg | I-A$_\beta^b$ (27) |
| | Lys | Tyr | Leu | Glu | Phe | Ile | Ser | Glu | Ala | Ile | Ile | His | Val | Leu | His | Ser | Arg | | | | Myoglobin (31) |

FIG.6

| | Source |
|---|---|
| Ile Ser Glu Ala Ile Ile His Val Leu His Ser Arg | Myoglobin (31) |
| Ile Ser Gln Ala Val  –  His Ala Ala His Ala Glu Ile Asn Glu | Ovalbumin (10) |
| Leu Glu Asp Ala    Arg Arg Leu Lys Ala Ile Tyr Glu Lys | λ Repressor cI (9) |
| Val Glu Asn Ala    Lys Lys Ile Glu Val Glu Phe Asp Lys | Nuclease (2) |
| Arg Glu Glu Ala Tyr His Ala Ala Asp Ile Lys Asp | Ragweed (35) |

FIG. 7

| SOURCE | |
|---|---|
| Ile Ala Tyr Leu Lys Gln Ala Thr Lys | Cytochrome c (35) |
| Leu Ala Tyr Ile Tyr Ala Asp Gly Lys | Nuclease (2) |
| Leu Lys Ala Ile Tyr Glu Lys Lys Lys | λ Repressor cI (9) |
| Ile Thr Ala Ser Val Asn Cys Ala Lys | Lysozyme (12) |

Class I α2--2nd Domain

```
              95        105       115       125       135       145       155       165       175   180
H-2Kb    GSHTIQVISGCEVGSDGRLLRGYQQYAYDGCDYIALNEDLKTWTAADMAAL ITKHHWEQAGEAERLRAYLEGTCVEWLRRYLKNGNATLLRT
H-2Kd    GSHTFQRMFGCDVGSDWRLLRGYQQFAYDGRDYIALNEDLKTWTAADTAAL ITRRKWEQAGDAEYYRAYLEGECVEWLRRYLELGNETLLRT
H-2Kk    GSHTFQRMFGCDVGSDWRLLRGYEQYAYDGRDYIALNEDLKTWTAADMAAL ITKHHWEQAGDAERDRAYLEGTCVEWLRRYLQLGNATLPRT
H-2Kw29.7 GSHTIQRMYGCDVGSDGRLLRGYEQVAYDGCDYIALNEDLKTWTAADMAAL ITKHHWEQAGAAERRRAYLEGACVEWLSRHLKNGNATLLRT
H-2Db    GSHTLQQMSGCDLGSDWMAGDVESDGRLLRGYLQFAYEGRDYIALNEDLKTWTAADMAAQITRRKWEQSGAAEHYKAYLEGECVEWLHRYLKNGNATLLRT
H-2Dd    GSHTLQWMAGCDVESDGRLLRGYWQFAYDGCDYIALNEDLKTWTAADMAAQITRRKWEQAGAAERDRAYLEGEAEYYRAYLEGECVEWLHRYLKNGNATLLRT
H-2Ld    GTHTLQWMYGCDMGSDGRLLRGYFQFAYDGCDYIALNEDLKTWTFADMSSQITRRKWEQAGAAEYYRAYLEGECVEWLHRYLKNGNATLLRT
H-2Q7d   GSHTLQWMYGCDVGCKVGSDGRLLRGYLQYAYDGRDYIALNEDLKTWTAVDMAAQITRRKWEQAGAAEYYRAYLEGECVEWLRRYLQLGKETLLRT
H-2Q10b  GSHTLQWMYGCKVGSDGRFLRGYLQYAYDGRDYIALNEDLKTWTAADYAAIITRRKWEQAGIAEKDQAYLEGTCMQSLRRYLELGKETLLRT
H-2Q10q  GSHTIQVMYGCEVEFFGSLFRAYEQHGYDGQDYIALNEDLKTWTAADTAAEITRSKWEQAGAAEYYRAYLEAECVEWLRRYLELGKETLLRT
H-2T1ab  GSHTIGVMYGCEVEFFGSLFRAYEQHGYDGQDYIALNEDLKTWTAADMAAEITRSKWEQAGYTELRRTYLEAECVEWLRRYLELGKETLLRT
H-2T1ac  GSHTVQRMYGCDVGSDGRFLRGYHQYAYDGKDYIALKEDLRSWTAADMAAQITKHKWEAAHVAEQLRAYLEGPCKDSLLRYLENRKKTQECT
H-2T2    GSHTIQIMYGCDVGSDGRFLRGYHQYAYDGKDYIALKEDLRSWTAADMAAQITKRKWEAAHEAEQRAYLDGTCVEWLRRYLENRKKTQECT
H-2Aw24  GSHTI MYGCDVGSDGRFLRGYRQDAYDGKDYIALNEDLRSWTAADMAAQITKRKWEAAHVAEQQRAYLEGTCVDGLRRYLENGKETLQRT
H-2A28   GSHTI MYGCDVGSDGRFLRGYRQDAYDGKDYIAL SWTAA MAAQITQRKWEAAREAEQ RAYLEGTCVEWL R LENGKETLQRT
HLA-A2   ASHTLQSMYGCDVGPDGRLLRGHDQYAYDGKDYIALNEDLRSWTAANTAAQITQRKWEAAREAEQLRAYLEGLCVEWLRRYLKNGKETLQQG
HLA-A3   GSHIIQRMYGCDVGPDGRLLRGYDQHAYDGKDYIALNEDLRSWTAANTAAQITQRKWEAARRAEQRRVYLEGEFVEWLRRYLENGKETLQRA
HLA-B7   GSHTMQVMYGCDVGPDGPFLRGYEQHAYDGKDYIALNEDLRSWTAADMAAQITKRKWEAAKRAEQRRAEQRRVYLEGFVEWLRRYLENGKETLQRA
HLA-Cw3  GSHTLYRMSGCDLGPDGRLLRGYDQSAYDGKDYIALNEDLRSWTAADTAAQITQRKLEAARAADEKRAYKEGTCVEWKRRYKENGKETKQRA
HLA-12.4 GSHTFQTMFGCEVWADGRFFHGYRQYAYDGADYIALNEDLRSWTAADTAAQNTQRKWEAAGEAERHRAYLERECVEWLRRYLEMCKETLQRA
HLA-328  GSHTLQWMYGCEVGADGRLLRGYEQFAYDGADYIALNEDLRSWTAADTTAQISKRKSEQASEAEHHRSYLEGECVEWLRRYLEDGKETLQRA
RLA-1
RLA-2
```

FIG. 9-2

Class II — α1 Domain

```
                 5        10        15        20        25        30        35        40        45        50        55        60        65        70        75        80        85
H-2Ab      EDDIEADHVGTYGISVYQSPGDIGQYTFEFDGDELFYVDLDKKETVWMLPEFGQLASFDPQGGLQNIAVVKHNLGVLTKRSNSTPATN
H-2Ad      EDDIEADHVGTYGVYQSPGDIVYQSPGDIGQYTFEFDGDELFYVDLDKKETVWRLPEFGQLILFEPQGGLQNIAAEKHNLGILTKRSNFTPATN
H-2Af      EDDIEADHVGFYGISVYQSPGDIGQYTFEFDGDEWFYVDLDKKETVWRLPEFGQLTSFDPQGGLQEIATGKHNLGIWTKRSNFTPATN
H-2Ak      EDDIEADHVGSYGITVYQSPGDIGQYTFEFDGDELFYVDLDKKETVWMLPEFAQLRRFEPQGGLQNIATGKHNLEILTKRSNFTPATN
H-2Aq      EDDIEADHVGSYGIVVYQSPGDIGQYTHEFDGDEWFYVDLDKKETVWMLPEFGQLTSFDPQGGLTKNIATGKHNLGGLTKRSNFTPAAN
H-2Ar      EDDIEADHVGVYGTTVYQSPGDIGQFTHEFDGDEWFYVDLDKKETIWMLPEFGQLTSFDPQGGLQNIAVVKHNLEILTKRSNFTPAAN
H-2As      EDDIEADHVGVYGTTVYQSPGDIGQYTHEFDGDEWFYVDLDKKETIWMLPEFAGLRSFDPQGGLQNIATGKYTLGILTKRSNSTPATN
H-2Au      EDDIEADHVGSYGIVYQS GPSGQYSHEFDGDELFYVDLDKKETVWQLPLFRRFRRFDPQFALTNIAVLKHNLLIVIKRSNSTAATN
HLADQα(1)  ED-IVADSVAQLGVNLYQS GPSGQYSHEFDGDELFYVDLERKETVWKLPLFHRL-RFDPQFALTNIAVLKHNLNLLIKRSNSTAATN
HLADQα(2)  ED-IVADHVASYGVNLYQSVGPSGQYTHEFDGDEEFYVDLERKETVWQLPLFHRL-RFDPQFALTNIAVLKHNLNSLIKRSNSTAATN
HLADQα(3)  ED-IVADHVASYGVNLYQSVGPSGQYTHEFDGDEEFYVDLERKETVWQLPVLRQF-RFDPQFALTNIAVLKHNLNIVIKRSNSTAATN
HLADQα(4)  ---ADHVASYGVNLYQSYGPSGQYSHEFDGDEFYVDLERKETVWQLPLFRRFRREDPQFDPQGAL NMAVAKHNLNIMIKRYNSTAATN
HLADQα(5)  ED-IVADHVASCGVNLYQFYGPSGQYTHEFDGDEFYVDLERKETAWRWPEFSKFGGFDPQGSALRNMAVGKHTLEFMMRQSNSTAATN
HLADQα(6)  ED-IVADHVASYGVNFYQSHGPSGQYTHEFDGDEFYVDLETKETVWQLPMFSRFISFDPQSALANIAVDKANLDVMKERSNNTPDAN
H-2Ed      ---IKEEHTII-QAEFYLLPDKRGEFMFDFDGDEIHVDIEKSETIWRLEEFAKFASFEAQGALANIAVDKANLDYMKERSNNTPDAN
H-2Ek      ---IKEEHTII-QAEFYLLPDKRGEFMFDFDGDEIHVDIEKSETIWRLEEFAKFASFEAQGALANIAVDKANLDYMKERSNYTPITN
HLADRα(1)  ---IKEEHVII-QAEFYLNPDQSGEFMFDFDGDEIFHVDMAKKETVWRLEEFGRFASFEAQGALANIAVDKANLEIMTKRSNYTPITN
HLADRα(2)  ---IKEEHVII-QAEFYLNPDQSGEFMFDFDGDEIFHVDMAKKETVWRLEEFGRFASFEAQGALANIAVDKANLEIMTKRSNYTPITN
HLADRα(3)  ---IKEEHVII-QAEFYLNPDQSGEFMFDFDGDEIFHYDMAKKETVWRLEEFGRFASFEAQGALANIAVDKANLEIMTKRSNYTPITN
HLADRα(4)  -------II-QAEFYLNPDQSGEFMFDFDGDEIFHVDMAKKETVWRLEEFGRFASFEAQGALANIAVDKANLEIMTKRSNYTPITN
HLADRα(5)  ---IKEEHVII-QAEFYLNPDQSGEFMFDFDGDEEQLSYDLLFSYDLFSYDLKKSEAVWRLPEFGDFARFDPQGBLAGIAAIKAHDILVERSRAIN
HLADZα     TKADMGSYGPAFYQSYGASGQFTHEFDEDEMPYVDLDKKETVWHLEEFGQAFSFEAQGGLANIAILNNNLNTLIQRSNHTQATN
HLADPα(1)  ---IKADHVSTY-AAFVQTHRPTGEFMFEFDEEEQFYVNLDEKEMVWPLPEFIHTFDFGAQRGIAGIVMARKHLNTRINC-KQTWATN
HLADPα(2)  ----DHVSTY-AEFVQTHRPSGEYMFEFDEEEQFYVNLDEKEMVWPLPEFIHTFDFGAQRGIAGIVMARKHLNTRING-KQTWATN
```

FIG. 10-1

Class II -- α2 Domain

|  | 90 | 95 | 100 | 105 | 110 | 115 | 120 | 125 | 130 | 135 | 140 | 145 | 150 | 155 | 160 | 165 | 170 | 175 | 180 |
|---|---|---|---|---|---|---|---|---|---|---|---|---|---|---|---|---|---|---|---|

```
H-2Aαb       EAPQATVFPKSPVLLGQPNTLICFVDNIFPPVINITWLRNSKSVADGVYETSFFVNRDYSFHKLSYLTFIPSDDDIYDCKVEHWGLEEPVLKHW
H-2Aαd       EAPQATVFPKSPVLLGQPNTLICFVDNIFPPVINITWLRNSKSVTDGVYETSFLVNRDHSFHKLSYLTFIPSDDDIYDCKVEHWGLEEPVLKHW
H-2Aαf       EAPQATVFPKSPVLLGQPNTLICFVDNIFPPVINITWLRNSKSVTDGVYETSFFVNRDYSFHKLSYLTFIPSDDDIYDCKVEHWGLEEPVLKHW
H-2Aαk       EAPQATVFPKSPVLLGQPITLICFVDNIFPPVINITWLRNSKSVTDGVYETSFLVNRDHSFHKLSYLTFIPSDDDIYDCKVEHWGLEEPVLKHW
H-2Aαq       EAPQATVFPKSPVLLGQPNTLICFVDNIFPPVINITWLRNSKSVTDGVYETSFFVNRDHSFHKLSYLTFIPSDDDIYDCKVEHWGLEEPVLKHW
H-2Aαr       EAPQATVFPKSPVLLGQPNTLICFVDNIFPPVINITWLRNSKSVTDGVYETSFLVNRDHSFHKLSYLTFIPSDDDIYDCKVEHWGLDEPVLKHW
H-2Aαs       EAPQATVFPKSPVLLGQPNTLICFVDNIFPPVINITWLRNSKSVTDGVYETSFLVNRDHSFHKLSALTFIPSDDDIYDCKVEHWGLEGPVLKHW
H-2Aαu       EAPQATVFPKSPVLLGQPNTLICFVDNIFPPVINITWLRNSKSVADGVYETSFLVNRDYSFHKLSALTFIPSDDDIYDCKVEHWGLEGPVLKHW
RT1Aα        ----------QPNTLICFVDNIFPPVINITWLRNSKPVTEGVYETSFLSNPDHSFHKMAYLTFIPSNDDIYDCKVEHWGLEEPVLKHW
HLADQα(1)    EVPEVTVFSKSPVTLGQPNTLICLVDNIFPPVVNITWLSNGHSVTEGVSETSFLSKSDHSFFKISYLTFLPSADEIYDCKVEHWGLDEPLLKHW
HLADQα(2)    EVPEVTVFSKSPVTLGQPNTLICLVDNIFPPVVNITWLSNGHSVTEGVSETSFLSKSDHSFFKISYLTFLPSADEIYDCKVEHWGLDEPLLKHW
HLADQα(3)    EVPEVTVFSKSPVTLGQPNILGEPNILICFIDKFSPPVVNITWLSNGHSVTEGVSETSFLSKSDHSFFKISYLTFLLPSAEESYDCKVEHWGLDKPLLKHW
HLADQα(4)    EVPEVTVFSKSPVTLGQPNILGEPNILICFIDKFSPPVVNITWLSNGHSVTEGVSETSFLSKSDHSFFKISYLTFLPSDDEIYDCKVEHWGLDEPLLKHW
HLADQα(5)    EVPEVTVFSKSPVTLGQPNILGEPNILICFIDKFSPPVVNITWLSNGQSVTEDVSETSFLSKSDHSFFKISYLTFLPSADEIYDCKVEHWGLDEPLLKHW
HLADQα(6)    EVPEVTVFSKFPVTLGQPNILGEPNILICFIDKFSPPVVNITWLSNGHSVTEGVSETSFLSKSDHSFFKISYLTFLPSADEIYDCKVEHWGLDQPLLKHW
H-2Eαd       VAPEVTVLSRSPVNLGEPNILICFIDKFSPPVVNVTWLRNGRPVTEGVSETVFLPRDDHLFRKFHYLTFLPSTDDFYDCEVDHWGLEEPLRKAW
H-2Eαk       VAPEVTVLSRSPVNLGEPNILICFIDKFSPPVVNVTWLRNGRPVTEGVSETVFLPRDDHLRFKFHYLTFLPSTDDFYDCEVDHWGLEEPLRKHW
RT1Eα        VIPEVTVLPKSPVNLGEPNILICFIDKFSPPAVNVTWLRNGQPVTKGVSETVFLPREDHLFRKFHYLTFLPSVEDYYDCEVDHWGLEEPLLKHW
HLADRα(1)    VPPEVTVLTNSPVELREPNVLICFIDKFTPPVVNVTWLRNGKPVTTGVSETVFLPREDHLFRKFHYLPFLPSTEDVYDCRVEHWGLDEPLLKHW
HLADRα(2)    VPPEVTVLTNSPVELREPNVLICFIDKFTPPVVNVTWLRNGKPVTTGVSETVFLPREDHLFRKFHYLPFLPSTEDVYDCRVEHWGLDEPLLKHW
HLADRα(3)    VPPEVTVLTNSPVELREPNVLICFIDKFTPPVVNVTWLRNGKPVTTGVSETVFLPREDHLFRKFHYLPFLPSTEDVYDCRVEHWGLDEPLLKHW
HLADRα(4)    VPPEVTVLTNSPVELREPNVLICFIDKFTPPVVNVTWLRNGKPVTTGVSETVFLPREDHLFRKFHYLPFLPSTEDVYDCRVEHWGLDEPLLKHW
HLADRα(5)    VPPEVTVLT SPVELREPNVLICFIDKFTPPVVNVTWLRNGKPVTTGVSETVFLPREDHLFRKFHYLPFLPSTEDVYDCRVEHWGLDEPLLKH-
HLADZα       VPPRVTVLPKSRVELGQPNILICIVDNIFPPVINITWLRNGQTVTEGVAQTSFYSQPDHLFRKFHYLPFVPSAEDVYDCQVEHWGLDAPLLKHW
HLADPα(1)    DPPEVTVFPKEPVDLGQPNILVCHIDKFFPPVLNVTWLCNGELVTEGVAESLFLPRIDYSEHKFHYLTFYPSAEDFYDCKVEHWGLDQPLLKHW
HLADPα(2)    APTEVSVFPKEPVDLGQPNTLVCHVDKFFPPVLNITWLRNGEPVIEGIAETIFLPSKKLRLHRFHYLTLVPMAEDTCDDQGEHWGLHQPLLRHW
```

IMMUNOMODULATING COMPOSITIONS AND THEIR USE

RELATED APPLICATIONS

This is a continuation-in-part of Application Ser. No. 066,812, filed June 25, 1987, now abandoned, which is a continuation-in-part of Application Ser. No. 017,343, filed Feb. 20, 1987, now abandoned, which is a continuation-in-part of Application Ser. No. 924,286, filed Oct. 29, 1986, now abandoned, and Application Ser. No. 880,134, filed June 30, 1986, now abandoned, all of which are incorporated herein by reference.

INTRODUCTION

1. Technical Field

Methods and compositions in immunology, where the immune system may be activated or deactivated in relation to particular transplantation antigens and T-cells. The methods and compositions involve vaccination, organ transplants, autoimmune diseases, pathogenic infections, as well as other health status situations which involve the immune system.

2. Background of the Invention

Vertebrates have developed a sophisticated system to protect themselves against a wide variety of hazards, viruses and various microorganisms, such as bacteria and fungii, genetic diseases, neoplasia, and the effect of a variety of toxins. The system has evolved based on the ability to recognize self as distinct from non-self. A broad panoply of defense mechanisms are involved, including phagocytosis, lysis, such as complement mediated or perforin mediated, killer T-cells, such as cytotoxic-T-lymphocytes, natural killer cells, antibody dependent cytotoxic cells, and the like. Various types of cells have different mechanisms whereby the invader or endogenous diseased cell may be eliminated.

A key to the immune defensive mechanism is the T-cell. T-cells have been found to be restricted in that they respond to an antigen in relation to one or a few specific transplantation antigens associated with their natural host. In vitro, T-cells from one haplotype host respond to an antigen in relation to a transplantation antigen of a different haplotype host. The T-cell receptor repertoire appears to be narrower than the B-cell immunoglobulin repertoire. In addition, rather than directly binding to the antigen, the T-cell receptor appears to require concomitant binding to an antigenic epitope and a transplantation antigen.

The transplantation antigens are divided into two classes, Class I and Class II, where the former class of antigens is relatively ubiquitous on host cells, while the latter class is relatively limited to lymphocytes, macrophages, and dendritic cells. Different T-cells appear to be activated in relation to one or the other class of transplantation antigen. In the main, the nature of the activity of a T-cell will vary with the class of the transplantation antigen to which it is complementary.

In effect it appears that a T-cell clone recognizes a specific antigen in conjunction with a specific transplantation antigen allele. Furthermore, variation in the antigen sequence, affects the nature of the response when the T-cell, antigen, and antigen presenting cell are brought together in culture. Depending upon the nature of the change, all three possibilities are encountered, namely, no change, increased stimulation or decreased stimulation.

In view of the above described events, it would be of substantial interest to be able to modify the immune response in vivo and in vitro, where one could provide stimulation or inactivation of a particular immune response. In this manner, the natural response to a particular event could be modulated, either by activating particular lymphocytes to enhance the protective response or by deactivating particular lymphocytes to diminish or prevent an immune response. By employing the immune system as the source of protection, a more holistic approach to medicine and disease can be achieved.

RELEVANT LITERATURE

Review articles that demonstrate the extraordinary progress and rate at which an understanding of T-cell restriction and the immune system has occurred is shown by Berzofsky, *The Year in Immunology* (1986) 2:28–38: Schwartz, *Ann. Rev. Immunol.* (1985) 3:237–261: Shastri et al., *J. Exp. Med.* (1986) 164:882–896. See also Shastri et al. ibid (1985) 162:332–345: Unanue and Allen, *Science* (1987) 236:551–557: Guillet et al., *Science* (1987) 235:865–870 (which discloses a portion of the work described in the subject application).

References of interest concerned with peptide analogs and an understanding of the interaction between Ia gene products, antigenic fragments, and T-cell receptors, may be found in DeLisi and Berzofsky, *Proc. Natl. Acad. Sci. U.S.A.* (1985) 82:7048–7052: Watts et al., *Proc. Natl Acad. Sci. U.S.A.* (1985) 82:5480–5484: Schwartz et al., *J. Immunol.* (1985) 135:2598–2607: Babbitt et al., *Nature* (1985) 317:359–361: Gammon et al., *Nature* (1986) 319:413–415: Babbitt et al., *Proc, Natl Acad. Sci. U.S.A.* (1986) 83:4509–4513: Watts et al., *Nature* (1986) 320:179–181: Finnegan et al., *J. Exp. Med.* (1986) 164:897–910: Lechler et al., *J. Exp. Med.* (1986) 163:678–696: Ashwell and Schwartz, *Nature* (1986) 320:176–179: Townsend et al., *Cell* (1986) 44:959–968: Shimonkevitz et al., *J. Immunol.* (1984) 133:2067–2074: Berkower et al., *J. Immunol.* (1986) 136:2498–2503.

Bastin et al., *J. Exp. Med.* (1987) 165:1508–1523; and Hirayama et al., *Nature* (1987) 327:426–430.

Other references of interest include Rock and Benacerraf, *J. Exp. Med.* (1984) 160:1824–1829 Rock and Benacerraf, ibid (1983) 157:1618–1634: Rao et al., *Cell* (1984) 36:889–895: Berkower et al., *J. Immunol.* (1984) 132:1320–1378: Ashwell et al., ibid (1986) 136:389–395: Mengle-Gaw and McDevitt, *Proc. Natl. Acad. Sci. U.S.A.* (1983) 80:762–765: Werdelin, *J. Immunol.* (1982) 129: 883–1891; Choi et al., *Science* (1983) 222:283–286 Lakey et al., *Eur. J. Immunol.* (1986) 16:721–727: Marx, *Science* (1987) 235:843–844: Kaiser and Kezdy, *Science,* (1984) 223:249–254.

See also U.S. Pat. Nos. 4,599,230 and 4,469,677. Other patents of interest include U.S. Pat. Nos. 4,473,555: 4,478,823: and 4,565,696.

SUMMARY OF THE INVENTION

Methods and compositions are provided comprising oligopeptides having defined contiguous and/or non-contiguous amino acid sequences for enhanced affinity of immunogens restricted by one or more transplantation antigens. Oligopeptides are prepared which can be used to modulate an immune response when a lymphocytic system is contacted with one or more antigens. The compositions employed may have a single oligopeptide or mixture of oligopeptides, so that a single compostion may be used with one or more cellular

BRIEF DESCRIPTION OF THE DRAWINGS

FIG. 5 shows the amino acid sequences of peptides restricted by the I-E$^d$ Class II molecule. Myoglobin P135-147) is recognized by I-E$^d$—restricted T-cell clones. Nuclease from *Staphylococcus aureus* (P66-78) is recognized by H-2$^d$ restricted T-cell clones. cI protein from lambda repressor (P12-24) I-E$_B^d$ sequence (69-81) I-E$_B^k$ sequence (69-81). Hemagglutinin from influenza virus (P111-120) is recognized by I-E$^d$ restricted T-cell hybridomas. I-E$_B^d$ sequence (28-36). I-E$_B^k$ sequence (28-36 ).

Figure 1:
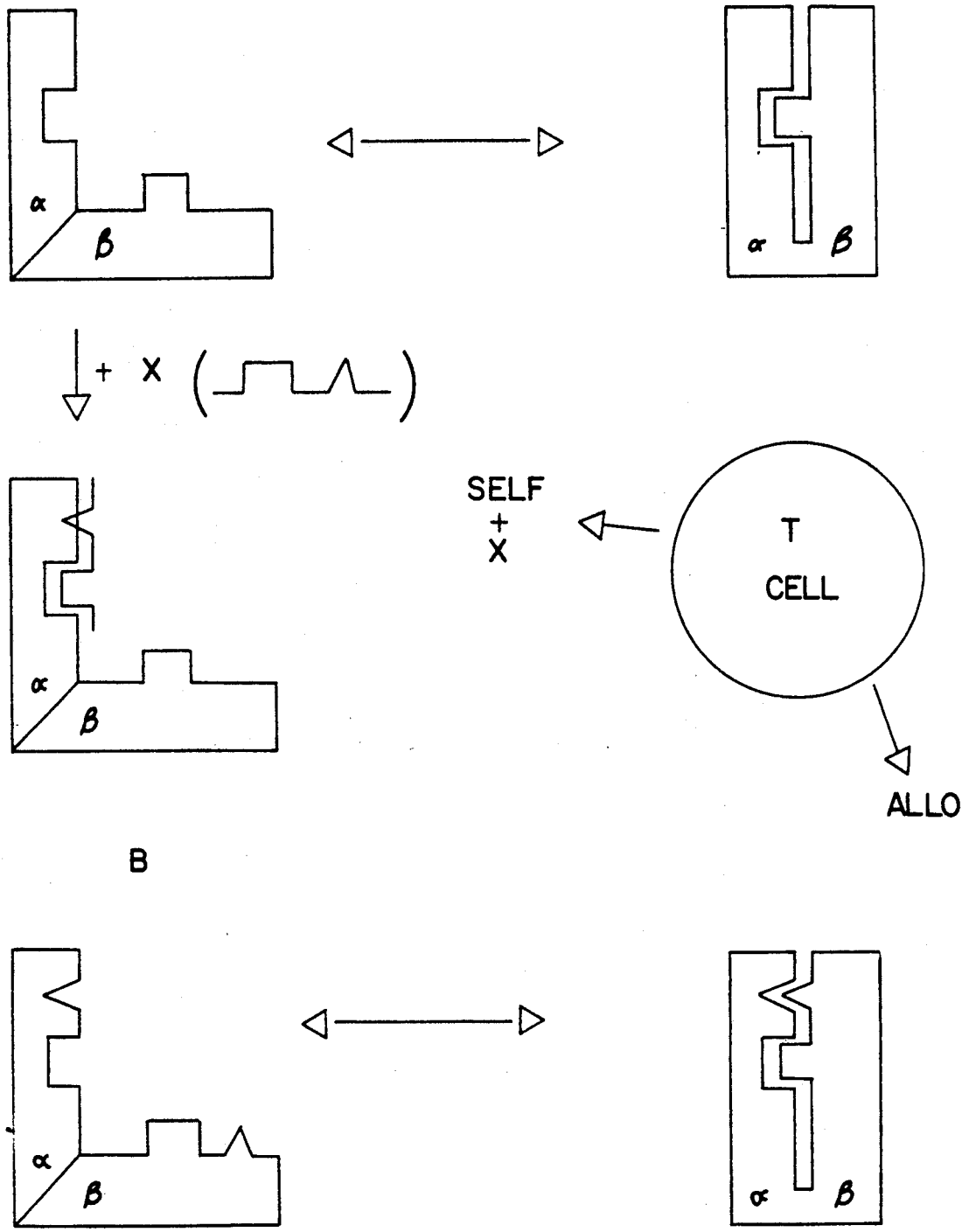
FIG. 1 is a schematic representation of the internal complementarity, consisting of an external receptor and an internal ligand, which is associated with domains of the transplantation antigen.

Numbers in parenthesis represent the amino acid residue positions in either the immunogen or the Ia molecule. Leu in parenthesis means that leucine and phenylalanine at the first position of peptide 111 to 120 from hemagglutinin are equivalent for stimulation of the hemagglutinin-specific I-E$^d$-restricted T-cell clone. The underlined residues show identity between the antigens and I-E$_B^d$ protein regions.

FIG. 6 shows a comparison of a partial amino acid sequence of ovalbumin and myoglobin with Class II antigen amino acid sequences. Ovalbumin (P326-339) is recognized by DO-11.10. I-A$_B^b$ sequence (42-55). Myoglobin (P102-118). Numbers in parenthesis represent the amino acid residue position in the native molecule.

FIG. 7 shows the amino acid sequences of 5 peptides restricted by the I-A$^d$ Class II molecule: myoglobin (P106-118): ovalbumin (P323-336): lambda repressor cI (P12-26): nuclease from *Staphylococcus aureus* (P66-80) and ragweed allergen (P54-65). Numbers in parenthesis represent the amino acid residue positions in the immunogen molecule. A dash represents a deletion at that location compared to the peptide above.

FIG. 8 shows the amino acid sequences of 4 peptides restricted by the I-E$^k$ Class II molecule: moth cytochrome (P95-103): nuclease from *Staphylococcus aureus* (P89-97): cI protein from lambda repressor (P18-26) and hen egg white lysozyme (P88-96). Numbers in parenthesis represent the amino acid residue positions in the immunogen molecule.

FIGS. 9-11 give the amino acid sequences of mouse, rat, rabbit and man Class 1, first and second domains; Class 2, α1 and α2 domains and; Class 2, β1 and β2 domains, respectively.

DESCRIPTION OF THE SPECIFIC EMBODIMENTS

Novel oligopeptides are provided, as well as their use in modulating the immune response of a lymphocyte system to an epitope, normally associated with a hapten or antigen. The oligopeptides are designed so as to have a greater affinity for one or more transplantation antigen as compared to an immunogen of interest, immunologically cross-reactive with the epitope. The oligopeptide sequence may be a fragment of a enhance or diminish the immune response to a particular immunogen. The oligopeptide including the agretope(s) and first epitope(s) may be joined to an antibody target sequence which may be considered as a second epitope, which may or may not bind the same T-cell receptor(s) bound by the first epitope. However, by virtue of the enhanced affinity of the agretope for the target transplantation antigen(s), an enhanced immune response will be obtained to the antibody target sequence. By employing various compositions, modified as indicated above, the immune response of a lymphocyte system may be modulated, by being deactivated or activated toward one or more particular immunogens.

The immune response which is modulated is predicated upon a ternary complex, involving a cell having a transplantation antigen, a T-cell receptor restricted by the transplantation antigen, and a polypeptide which specifically binds to the combination of transplantation antigen and T-cell receptor. The transplantation antigens may be divided into two classes, Class I and Class II. Class I is relatively ubiquitous, found on most cells of a mammalian host, and has a polymorphic α-chain and a conserved β-chain. By contrast. Class II transplantation antigens are restricted to relatively few sets of cells, primarily lymphocytes macrophages, and dendritic cells, and comprise polymorphic α- and β-chains. In the case of Class I transplantation antigens, one is primarily concerned with cellular aberrations or diseased states, such as viral infection, mycoplasma infection, neoplasia, or the like, or with organ transplants. The T-cells involved will normally cause the destruction of the aberrant cell.

By contrast, Class II transplantation antigens are concerned with activation of the cellular immune system, resulting in the expansion of cells involved with protection of the host against aberrant physiological states. The aberrant physiological states may be involved with pathogenic invasions, including viruses, bacteria, fungii, protista, toxins, or the like. In addition, the Class II cells may be involved with various autoimmune diseases, such as rheumatoid arthritis, systemic lupus erythematosus, diabetes, etc., as well as those cellular aberrations or diseased states associated with Class I transplantation antigens.

Class I transplantation antigens are also involved in rejection of organ transplants. The immune system is able to recognize the foreign nature of the transplantation antigens present on the transplanted organ and attack the organ. In this situation, one does not wish to protect the host from the foreign cells, but rather diminish the subset of the immune system which is specific for attacking the organ transplant.

In many situations, there will also be interest in controlling lymphocyte response in vitro. These situations may involve specifically destroying cells infected with mycoplasma or virus, removing a particular subset of cells from a mixture of neoplastic and normal cells, expanding a particular subset or subsets of cells in the mixture, providing for conditioned medium for production of various lymphokines, such as IL-2, or the like. The in vitro system may involve whole blood, plasma, serum, cellular fractions, normal or immortalized cells, etc.

The manner in which the oligopeptide is defined is in relation to the transplantation antigen sequence, the polymorphic region, and the immunogens restricted by the transplantation antigen. The sequence of the transplantation antigen may be defined by comparing homology between the immunodominant sequences of antigens restricted by the transplantation antigen, where included in the comparison may or may not be the polymorphic region of the transplantation antigen. (For a discussion of the immunodominant sequence see, for example, Berzofsky, (1986) supra, and references cited therein.)

Transplantation antigens have polymorphic regions, where the individual alleles are associated with specific hosts. For the most part, the host will be diploid and heterozygous, so that each host will have two haplotypes, meaning that there will be two different copies of a particular transplantation antigen type from the same locus, unless the host is homozygous at that particular locus.

The homology of the immunodominant sequences may be compared using the FASTP algorithim, although any other algorithim which allows for comparison of homology may be employed. For a description of FASTP, see Lipman and Pearson, *Science* (1985) 227:1435–1441. The immunodominant sequences should have about 30% homology or greater, with up to a total of 20%, usually not more than about 15% based on the number of amino acids in the sequence of deletions or insertions to provide for the desired homology. That is one counts the non-conservative substitutions first, then deletions and insertions to provide the best homology. Desirably, the homology will involve identity, rather than conservative substitutions. Usually, there will be not more than a total of 2 amino acids involved in insertions or deletions, and usually not more than about 1 insertion or deletion, usually deletion.

The following table indicates conservative substitutions, where any amino acid on the same line may be substituted for any other amino acid on the same line.

| Amino Acids |
| --- |
| Aliphatic |
| non-polar |
| G, A, (P) |
| V, L, I |
| polar |
| neutral |
| C, M, S, T |
| N, Q |
| acidic |
| D, E |
| basic |
| K, L, (H) |
| aromatic |
| F, W, Y, (H) |

Proline (P) may be considered equivalent, but will normally not be substituted for the other amino acids on the same line. Similarly, Histidine (H) may be substituted for the other amino acids on the same line, but will not normally be considered an equivalent. In addition, in some instances, the acidic, basic, and polar amic amino acids (N, Q) may be substituted one for the other in determining homology.

Normally, at least 2 immunodominant sequences will be involved in the determination of a consensus sequence for an agretope, more usually 3 and not more than about 8 should suffice, usually 3 to 6 sequences will suffice. The immunodominant sequences may be identified in a number of ways. Particularly, the protein restricted by the transplantation antigen may be divided into a number of sequences, which may be synthesized and then used in an assay, where cells containing the particular transplantation antigen and T-cells restricted by the transplantation antigen and specific for the specific antigen are combined. (See Experimental section for assay.) By determining the level of secretion of IL-2 (interleukin-2), one can define the sequence which is immunodominant. Usually there will be a single immunodominant sequence, although in some antigens, there may be more than 1. However, where there is more than 1, both the sequences may be used in defining a consensus sequence for optimizing binding affinity to the particular transplantation antigen.

Usually, there will be not more than 7 amino acids involved with the agretope, more usually not more than 5 amino acids defining the agretope, normally at least 2 amino acids, more usually at least 3 amino acids. The amino acids may be in tandem or separated by from 1 to 4 amino acids, usually 2 to 4 amino acids. By comparing the homologies, particularly identities, desirably at least 2 identities, more desirably at least 3 identities, and the spacing of the consensus sequence, usually differing by not more than 1 amino acid, one can define a sequence which will have a higher affinity for the transplantation antigen than one or more, usually all of the antigens employed for the determination of the consensus sequence. Thus, the amino acids having homology will usually be 1-4, 4-8, or 6-12 amino acids apart, usually 2-3 or 4-9 amino acids apart, between any 2 amino acids, although tandem homologies may be encountered. Once the consensus sequence is defined, one may then scan any antigen restricted by the particular transplantation antigen to define the immunodominant region containing the agretope and the first epitope. The information concerning the sequence may then be used for immunomodulation of a lymphocytic system.

The oligopeptide comprising the agretope and epitope (oligo-a-e) will normally differ from a sequence present in the polymorphic region of the transplantation antigen to which it binds. It is found that there is a sequence in the polymorphic region which serves as an internal ligand to a receptor of the transplantation antigen. Thus, this region will have some homology to the immunodominant regions restricted by the transplantation antigen in many cases. However, the internal ligand will normally differ significantly from the consensus sequence, although sharing some moderate homology with the consensus sequence. By employing an oligo-a-e having the identical sequence to the internal ligand sequence of the transplantation antigen, one can substantially inhibit any T-cell response. The effect is as if the oligo-a-e is recognized as self, and either the ternary complex does not form or, if formed, the T-cell is not activated.

A number of antigens have been described in the literature, where particular sequences have been described as antibody producing and useful in production of antibodies for protection of hosts against particular pathogens or toxins. These compositions will for the most part be less than about 5 kD. usually less than about 3 kD, so that they would normally be considered haptenic. These sequences may be used as the antibody target sequence and be joined to an oligo-a-e. The resulting molecule will have two domains to form a novel polypeptide where each domain will be fewer than about 70% of the total molecule, usually the oligo-a-e agretope-containing domain being from about 30 to 70% and the antibody target sequence domain being from about 10 to 60%.

For the most part, the oligo-a-e agretopecontaining domain will vary from about 8 to 30 amino acids, more usually from about 8 to 20 amino acids, while the antibody target sequence domain will vary from about 5 to 25 amino acids, more usually from about 5 to 20 amino acids.

The agretope-containing domain may be selected in a variety of ways. One may use a universal oligo-a-e, where the first epitope may be also selected in a variety of ways. One may select the first epitope arbitrarily, insuring that it is not identical with the transplantation polymorphic region in a majority of the hosts with which it will be used. Alternatively, it may be selected so as to have an epitopic site associated with an innocuous epitope, such as already indicated, e.g. tetanus toxoid, keyhole limpet hemocyanin, bovine gamma-globulin, BCG, human gammaglobulin, or portions of cell endogenous proteins, etc. Finally, it may have an epitope of interest which shares some relationship with the purpose for which the antibody target sequence is being employed, e.g. the first epitope may be an epitope different from the antibody target sequence but present on the same antigen or a different antigen associated with the antigen of the antibody target sequence. For example, in the case of a virus, the first epitope and antibody target sequence could be present on the same or different capsid proteins, envelope proteins, etc. Particular antibody target sequences of interest include neutralizing antibody target sequences (epitopes) of pathogenic microorganisms, e.g. bacteria and viruses.

The oligopeptides employed in this invention which define immunodominant regions and are not joined to heterologous sequences (that is sequences other than the natural sequence to which they are normally joined), will not include cytochrome c, ovalbumin, myoglobin, nuclease from *Staphylococcal aureus*, lysozyme, repetitive sequences of 1, 2, and 3 amino acids, influenza hemagglutinin, naturally occurring hormones of fewer than about 20 amino acids, such as oxytocin, bradykinin and angiotensin, herpes glycoprotein d, insulin, particularly bovine insulin B-chain, ragweed allergen Ra3, human ACh receptor-γ, VP1 foot-mouth virus, angiotensin 2, fibrinopeptide B-14, minimum stimulatory polymer, HLA CW3, myelin basic protein, particularly rat and guinea pig, rabies glycoprotein, flu matrix protein, tuberculosis 65 kd protein, or other oligopeptide prepared prior to the effective filing date of the subject application.

As already indicated, the agretope will normally have greater binding affinity to the transplantation antigen than the antigen of interest, so that the oligo-a-e may successfully compete with the antigen of interest in forming the ternary complex. The antigen of interest is the antigen(s) to which the immune system is being modulated. The oligo-a-e sequence may be the total sequence of a molecule, or only a portion of a much larger peptide. The oligo-a-e may be joined in a variety of ways to the second epitope For in vivo purposes, there will be a target antigen of interest to which the host may be or is exposed. For example, where a close match has been made between a donor and recipient of an organ transplant, there may be only a few antigenic sequences or epitopes present on the organ which could result in a strong immune response. In accordance with the subject invention, one would block the T-cells which respond to the immunodominant regions of such antigens to diminish the rejection response by the host. In another situation, where an individual would be entering an area in which a parasite is prevalent, the individual would be vaccinated with an oligopeptide having one or more antibody target sequence(s) cross-reactive with the parasitic antigen(s) to provide cellular and humoral protection. These and many other situations will be served by the subject invention. In preparing oligopeptides for the different situations, various strategies will be employed.

One composition would have the antigen of interest mutated at the immunodominant site to enhance the affinity of the antigen of interest for one or more transplantation antigens present in the host. Particularly, with B-cells and Class II transplantation antigens, the various epitopes of an immunogen of interest will bind to the surface immunoglobulin of the B-cells present in the lymphocyte system, whereby the immunodominant sequence will then bind to the transplantation antigen and be presented to the T-cell recognizing the particular immunodominant sequence. Because of the higher binding affinity, an enhanced immune response would be achieved. By employing the mutated immunogen, a plurality of B-cells may be activated in conjunction with T-cells having a T-cell receptor which recognizes the particular immunodominant region.

Alternatively, one may solely use the mutated immunodominant region, whereby only a few B-cells will be activated which bind to the immunodominant region in conjunction with the particular T-cell. Another alternative is to select one or more epitopic sites present on the antigen to which the immunodominant region may be joined, either directly or through a bridge, usually having fewer than about 50 amino acids, more usually having fewer than about 30 amino acids. In this manner, a single fused protein may be obtained, where the immunodominant region is fused to one or more epitopic sites of interest.

Rather than having a fused protein, one may join the immunodominant region by linking the immunodominant region to a peptide of interest. The linkage may take a variety of forms, the particular manner of linkage not being critical. Thus, one can provide for a cysteine to be present at a terminus or other site of the oligopeptide, where the antigen of interest may be functionalized with a maleimide group. By combining the cysteine modified immunodominant sequence with the functionalized antigen, a thioether linkage may be achieved. If appropriate, a carboxyl group present on the immunodominant sequence may be activated, using carbodiimide, or forming an active ester, e.g. p-nitrophenyl ester, where any available amino groups present on the oligopeptide are blocked. After reacting the oligopeptide with the antigen of interest to form a peptide bond, the blocking groups may be removed. Other techniques may also be employed, as described by Fieser and Fieser, Reagents for Organic Synthesis, Vol. 3, Wiley-Interscience, N.Y., 1972.

The immunodominant region may be modified, not only as to the agretope, but also as to the first epitope to provide the oligo-a-e. Thus, one can modify the T-cell receptor which will recognize the immunodominant region, so that the immunodominant region may be recognized by more than one T-cell, or by different T-cells from the T-cell which recognize the wild-type immunodominant region. Particularly, where the immunodominant region is joined to an antibody target sequence, one may wish to modify the agretope, so as to either minimize any T-cell response or provide a T-cell response to a substantially immunologically unreactive epitope.

In this situation, the first epitope may be modified so as to mimic the epitope of a vaccine, such as tetanus toxoid or other relatively innocuous antigen such as previously described. Alternatively, one may modify the first epitope to a sequence to which there is no T-cell receptor which is activated. This may be considered to be a "hole in the repetoire," where a particular epitope finds no homologous T-cell receptor to bind. One might anticipate that those epitopes which mimic self-epitopes would provide this property, as well as other epitopes which will be discovered to specific haplotypes. Depending upon the desired result, various combinations of agretopes, first epitopes and antibody target sequences can be employed, to activate or inactivate particular subsets of B-cells and/or T-cells. Thus, one can selectively choose a single subset of T- or B-cells or groups of subsets of either or both T- or B-cells to modulate toward a specific purpose.

For example, if one wished to inactivate a specific subset of B-cells specific for a particular epitope, one would prepare a polypeptide having two regions. One region, the antibody target sequence, would involve an amino acid sequence which mimics the epitope of interest. The other region would be an oligo-a-e which would not provide for T-cell receptor binding, for example, an identical sequence to a sequence of the polymorphic region of the transplantation antigen(s) of the host of interest. In this situation, the resulting polypeptide would be bound by those B-cells which recognize the second epitope and be presented to the T-cell receptor under conditions which would block activation. Furthermore, the antibody target sequence would be selected so as to minimize the affinity of the epitope to the transplantation antigen. In this way, the T-cell will not be activated by the binding of the polypeptide to the transplantation antigen so that those B-cells which recognize the polypeptide will remain unstimulated by T-cells. If one wished to block any T-cell stimulation of B-cells a T-cell non-activating oligo-a-e could be used.

Where one wishes to stimulate a particular subset of T-cells, one would employ an agretope specific for a Class II transplantation antigen. In this situation, the first epitope would be chosen to be directed to the particular subset of T-cells of interest. In this manner, one could build up a T-cell population directed to a particular antigen, for example, as in the case of a neoplastic condition, in cases of autoimmune diseases, or the like.

For stimulating both B- and T-cells, one could employ an oligo-a-e with an epitope specific for the antigen of interest. In addition, one could employ the oligo-a-e joined to other epitopes of the same or associated antigens, so that a plurality of B-cells would be stimulated, where the different subsets of B-cells were specific for different epitopic sites. This situation would have application in a number of different situations. In addition, one could prepare an oligopeptide or protein having a plurality of oligo-a-e's, so that the same molecule would be effective for a plurality of transplantation antigens.

For example, in preparing a vaccine, one could provide for epitopes of different strains for a particular pathogen, e.g. virus or bacterium, so that B-cells recognizing all of the different strains would be stimulated at the same time, by virtue of a single molecule. One could also provide for epitopes of different molecules, where one wishes to vaccinate a host against a plurality of organisms, for example the TORCH series for pregnant women (Toxoplasmosis, Rubella, Cytomegalovirus, and Herpes Simplex virus). Therefore, particularly in those situations where a battery of antigens are involved, the subject methodology allows for a single molecule to provide for immunization against a plurality of epitopes associated with different organisms and for a plurality of transplantation antigens to be bound.

Usually, the number of different antibody target sequences will range from 0 to 20, more usually from about 0 to 10, conveniently from about 1 to 6. Each of the antibody target sequences will have at least about 5, usually 8 amino acids and not more than about 30 amino acids, more usually not more than about 20 amino acids. Depending upon the nature of the individual epitopes, the epitopes may be joined head-to-tail or may be separated by bridging groups of from about 1 to 30 amino acids, usually from about 1 to 20 amino acids. The bridging groups may be any convenient sequence, but will usually be subject to selection so as to avoid interference with the proper binding of the epitopic sequences and to avoid creating undesirable immune responses to epitopes which could be detrimental to the host.

The compositions of this invention may be a single polypeptide or a mixture of polypeptides, usually a mixture of polypeptides. Generally, the number, of polypeptides will not exceed about 20, more usually not exceed about 12, and preferably not exceed about 8, more preferably not exceed about 6. The mixtures will usually be directed to those transplantation antigens which are most frequently found in the population of interest. That is, particular transplantation antigens may be more frequent in certain population groups, for example, different species, such as humans, other primates, domestic animals, lab animals, etc. such as ovine, porcine, equine, avian, etc. By properly selecting agretopes which bind to the most common transplantation antigens, either or both Class I or Class II, there is the opportunity to minimize the total number of different polypeptides involved. Furthermore, in many situations, different transplantation antigens may share particular amino acids in the consensus sequence, so that higher or equivalent affinity as to the antigen(s) of interest, may be achieved with a number of transplantation antigens with a single oligo-a-e or consensus sequence.

For the most part, since most hosts will be heterozygous, if one wishes to involve more than one transplantation antigen allele, it will be desirable to have at least two molecules of different consensus sequences unless the two transplantation antigens have substantially similar consensus sequences, and up to 6 consensus sequences in humans.

The subject compositions may be formulated in a variety of ways for administation to a host or for use in vitro. They may be formulated in any convenient physiologically acceptable medium for administration to a host. These media include water, saline, phosphate buffered saline, oil emulsions, etc. In some instances it may be desirable to formulate the subject peptides as tablets, microcapsules, e.g. slow release, liposomes, gels, powders, precipitates, e.g. alum. or the like. In some situations, it may be desirable to provide for continuous infusion into the host, by employing convenient delivery systems, such as catheters, constant diffusion membranes, pumps, or the like. These formulations and techniques are well known in the literature. Administration may be by injection, for example, intravascular, peritoneally, subcutaneously, subtopically, intradermal patches, etc.

The amount of the subject compositions will vary widely depending upon the particular purpose, the manner of administration, the nature of the host, the duration of the treatment, the frequency of repetitive treatment, and the like. Thus, for the most part, with each composition, the amount used will be determined empirically. However, some general considerations can be made concerned with the administration of oligopeptides to a host. To that extent, the oligopeptides will generally range from about 0.01 to 10 µg/kg of host, where concentrations will generally range from about 10 µg/ml–1 mg/ml. Other additives may be included in the formulations, such as stabilizers, antibiotics, excipients, adjuvants, precipitates for adsorption, slow release additives, etc.

The subject polypeptides may be prepared by any convenient means. Usually, either chemical synthesis will be employed or recombinant techniques. For the most part, the polypeptides employed in this invention will have fewer than 200 amino acids, more usually fewer than 150 amino acids, preferably fewer than about 100 amino acids, and more preferably fewer than about 75 amino acids, generally ranging from about eight to 60 amino acids. However, as previously indicated, a wild-type or naturally occurring protein may be employed where the immunodominant region(s) have been mutagenized to change the transplantation antigen affinity.

Based on known techniques, one can synthesize genes encoding the subject compositions. Techniques for synthesizing oligodeoxynucleotide single strands are well established and strands may be obtained of 200 bases or more. By appropriately overlapping strands, large synthetic sequences can be prepared. Alternatively, where one has mutated the immunodominant sequence of an available antigen, various techniques are available for precisely introducing the mutation, such as in vitro mutagenesis, restriction and insertion of a synthetic sequence, or the like. The particular manner in which the mutation is carried out is not critical to this invention.

Once the gene has been obtained it may be used in accordance with conventional techniques for expression. A significant number of expression vectors are available commercially or in the literature, which may be used with advantage in the subject invention. The host transformed with the vectors may provide for stable extrachromosomal maintenance or integration into the host genome. Convenient expression hosts include *E. coli, B. subtilis, B. licheniformis, Saccharomyces,* e.g. *cerevisiae, Kluyveromyces,* e.g. lactis. Of primary interest will be mircoorganisms, particularly bacteria and fungii, e.g. yeast.

If desired, the constructs can be prepared in conjunction with known signal leaders for secretion. Signal leaders include the c-factor of yeast, α-amylase, penicillinase, surface membrane proteins, etc. The signal leader with its processing signal may be joined at the 5′ terminus of the gene, so as to provide for a fused precursor, which upon maturation loses the signal leader and processing signal.

The human transplantation antigens of interest as being the ones being generally encountered include for Class II: see Figueroa and Klein, *Immunology Today* (1986) 7:78–81, and references cited therein: for Class I: see Klein and Figueroa ibid (1986) 7:41–44, and references cited therein. The human Class II antigens, are divided into DP, DQ and DR, where the mouse H-LA (I-A) corresponds to HLA-DQ and the mouse H-LE (I-E) corresponds to DR. The different transplantation antigens may play different roles. As reported by Hirayama et al., supra, and references cited therein, suggest that suppressor T-cells (CD8+) are restricted by DQ while helper T-cells (CD4+) are restricted by DR. Using the relationship, either helper or suppressor cells may be stimulated to provide for immunomodulation of the immune response of a host to an epitope of an antigen.

Figure 4:
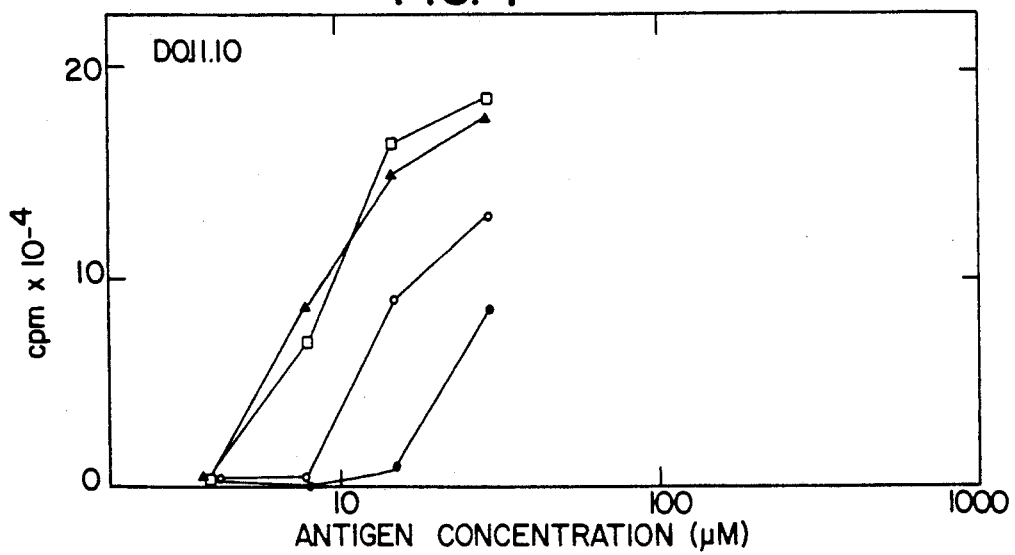
FIG. 4 is a graphic representation of the inhibition of activity of DO-11.10 T-cell hybridomas, when cultured with various concentrations of (P324-336) ovalbumin and A20 presenting cells in medium alone (◐-◐), in the presence of influenza hemagglutinin P111-120 (▲-▲) or P12-26 (○-○) or influenza hemagglutinin site 2 (P126-138) ( •-• ) each at 50 μM. The values shown represent the arithmetic mean in triplicate samples as explained in FIG. 2.

The first epitopes and antibody target sequences of interest will include surface membrane proteins, envelope proteins, capsid proteins, oncogenes, transplantation antigens, toxins, allergens, carbohydrates, polysaccharides, etc. Antigens associated with viruses will include such viruses as Herpes, Hepatitis, HIV, influenza, FeLV, Rhinoviruses, and other pathogenic viruses. Antigens associated with unicellular pathogens will include such organisms as *Plasmodium, Hemophilus, E. coli*, Salmonella, Tripanosomes, Pseudomones, and Toxoplasmosis and other pathogenic bacteria and parasites. Antigens associated with oncogenes will include such oncogenes as human fas, myc, abl, ras, etc. Antigens associated with toxins will include such toxins as aflatoxin, Diptheria, botulins, etc. A list of pathogens of interest may be found in U.S. Pat. No. 3,996,345.

A large number of epitopes have been defined for a wide variety of organisms of interest. Of particular interest are those epitopes to which neutralizing antibodies are directed. Disclosures of such epitopes are in many of the references cited in the Rele/ant Literature section.

The various epitopes may be joined to sequences having the consensus sequence for binding to the polymorphic regions of the transplantation antigens. Of particular interest are the regions involved with the Class II polymorphic domains $\beta$-2 and $\beta$-3 variable regions. In these domains, amino acids 20 to 40, and 65 to 85, more particularly 2 to 30 and 68 to 78 are of interest. Thus, the compositions which are prepared in accordance with this invention will be varied from these regions by having at least one mutation which enhances the affinity of the sequences for the transplantation antigen by including an amino acid associated with the agretope as defined by the consensus sequence.

Illustrative of vaccines is a vaccine involving an antibody target sequence for Plasmodium parasites, particularly falciparum. An antibody target sequence is prepared having at least three repeating units of the tetramer $(N\text{-}A\text{-}N\text{-}P)_n$, where n is at least 3 and usually not more than 12. This oligomer may be covalently bonded or fused to one or more oligo-a-e's having specific affinity for particularly host haplotypes. (For a description of the Plasmodium epitope, see Lavale, et al., *Science* (1985) 228:1436–1440; Miller et al., Science (1986) 234:1349–1356. The oligo-a-e(s) may be selected to have an innocuous first epitope and at least three, preferably at least four members of the consensus sequence as to each haplotype. The same strategy employed for preparing a malovia vaccine may be extended to other parasites and pathogens.

A domain of particular interest is the Class II third variable region, more particularly the amino acids 68 to 80. In this region, the polymorphic amino acids are L-E-D*-A*-R-A-S*-V-D-T-Y*-C-R, where the polymorphic sites have an *, so that the amino acid at that site may vary conservatively or nonconservatively.

The following examples are offered by way of illustration and not be way of limitation.

First, observations will be given, followed by the experimental protocols for obtaining the observations.

EXPERIMENTAL

T-cell hybridomas were obtained as described in Guillet et al., *Science* (1985) 235:865–870: and Lechler et al., *J. Exp. Med.* (1986) 163:678–696 (particularly references cited therein). The procedure for determining inhibition or activation is described in Guillet et al., supra.

Inhibition of antigen-specific T-cell activation by non-stimulatory peptide analogs Inhibition of antigen-specific T-cell activation by non-stimulatory peptide analogs was assessed, using the T-cell hybridoma 7B7.3 and the T-cell hybridoma 8I.

7B7.3 was derived from a Balb/c mouse immunized with the immunodominant peptide derived from bacteriophage lambda repressor, cI. It is stimulated with the peptide P15–26, which contains amino acid residues 15–26 of cI, in the context of I-$A^d$. The T-cell hybridoma 8I is derived from the A/J strain and recognizes the same peptide (P15–26), but in the context of I-$E^k$.

Neither 7B7.3 nor 8I can be stimulated by homologous peptide P12–24 (which contains residues 12–24 of cI). Other T-cells, however, derived from Balb/c mice, can recognize P12–24 in the context of I-$A^d$. This suggests that P12–24 can bind to the I-$A^d$ molecule but presumably cannot stimulate 7B7.3 because it lacks a specific T-cell interaction residue (an epitope). It was found that P15–26 dependent 7B7.3 activation would be inhibited when the peptide P12–24 was also included in the culture. See FIG. 2.

In the case of 7B7.3, P12–24 inhibited activation by P15–26 in a dose-dependent manner; the potency of the inhibition depended on the concentration of the inhibitor. P12–24 changed the apparent affinity of 7B7.3 for P15–26 (See Example II). The inhibitory effect was reversed by increasing the concentration of P15–26 in culture.

In contrast, the same peptide (P12–24) had no statistically significant effect on 8I activation, as demonstrated by IL-2 response of the hybridoma.

Inhibition of repressor-specific T-cell activation by other I-$A^d$-restricted peptides The competitive ability of peptides derived from two other antigen systems to inhibit P15–26 dependent activation of 7B7.3 was determined. For this purpose, peptides derived from Staphylococcus nuclease (Nase), residues 61–80 (P61–80) and from ovalbumin (Ova), residues 324–336 (P324–336) were used to inhibit cI P15–26 dependent activation of 7B7.3. Each is I-$A^d$-restricted and immunodominant for its respective antigen. This work is described in detail in Example III.

Results showed that 7B7.3 activation is inhibited, in a dose-dependent manner, by these peptides. Specificity is seen in that the same peptides are without significant effect on the I-$E^k$ restricted P12–26 specific T-cell, 8I.

Inhibition of ovalbumin-specific T-cell activation by other I-$A^d$-restricted peptides The T-cell hybridoma DO-11.10, is ovalbumin specific and I-$A^d$-restricted. It responds to the peptide P323–339 derived from ovalbumin. It responds less to the truncated analog P324–336. P324–336 peptide was used as stimulator. The lambda repressor cI peptide P12–26 and a peptide influenza hemagglutinin site 2 (I-A$^d$-restricted) were used as potential inhibitors. Neither of these can stimulate DO-11.10 on its own. As shown in FIG. 4, these non-stimulatory peptides act as inhibitors for ovalbumin-specific T-cell activation. The I-E$^d$ restricted influenza hemagglutinin-derived peptide P111–120 was used as a control and had no effect on ovalbumin-specific T-cell activation.

Results of this work demonstrated competitive inhibition of T-cell activation by unrelated peptides restricted by the same Class II molecule (I-A$^d$).

Binding of repressor peptide P12–26 to Class II molecules in vitro

The lambda repressor (cI) P12–26 peptide was labelled with $^{125}$I and tested for its ability to bind to various Class II molecules. It was observed that the peptide could bind to Class II molecules isolated from the d and k haplotypes, as shown in Table 1 (Example V). The I-A$^d$ and I-E$^k$ molecules are restricting elements for the peptide, but the I-A$^k$ and I-E$^d$ molecules are not.

The P12–26 peptide binds most tightly to the I-E$^d$ molecule, despite the fact that this molecule was never observed to act as a restricting element for P12–26-specific T-cells derived from Balb/c mice.

To determine whether the binding of P12–26 is specific for the I-E$^d$ molecule, its ability to compete for binding with a myoglobin-derived peptide, known to be restricted by (and to bind to) I-E$^d$ was examined. The binding is specific as shown in Table 2 (Example V).

P12–26 also competes with other immunodominant peptides for binding to their respective Class II molecules. Competition, however, is not observed for the lysozyme-derived peptide restricted by I-A$^k$, a Class II molecule which is not bound by P12–26 (see Table 1 of Example V). In fact, P12–26 binds best to the I-E$^d$ molecule, as shown by its relative binding ability as well as its relative competitive ability.

In view of this unexpected result, the presence of T-cells restricted by I-E$^d$ in the Balb/c mouse immunized with the NH$_2$-terminal domain of cI was re-examined.

There appears to be an absence of T-cells in cI immune mice able to recognize P12–26 in the context of the I-E$^d$ molecule there is apparently a hole in the repertoire with respect to P12–26 and the I-E$^d$ molecule.

Competition at the level of the I-a molecule

The immunodominant peptides derived from both Staphylococcal nuclease and ovalbumin are able to inhibit T-cell activation of a cI-specific T-cell hybridoma. The degree of inhibition observed is dependent on the ratio of stimulator to competitor, and, therefore, the inhibition with regard to the activator appears to be competitive in nature. Similarly I-A$^d$-restricted peptides are shown to inhibit the activation of an ovalbumin-specific T-cell hybridoma.

In order to observe inhibition of the P12–26specific T-cells 7B7.3, it was necessary to use the weakly stimulatory truncated analog, P15–26, as an activator. Similarly, for the Ovalbumin-specific T-cell, DO-11.10, a poorly stimulating peptide analog was used as activator.

Antigen peptides as analogs of self

In light of the fact that the cI peptide binds to both I-A$^d$ and I-E$^d$ and the Nase peptide can apparently be restricted by both Class II molecules and presumably also binds to both, the amino acid sequences of the two peptides were compared to those of other peptides restricted by either I-A$^d$ or I-E$^d$.

As shown in FIG. 5, the I-E$^d$-restricted, immunodominant peptide derived from sperm whale myoglobin bears a homology to both the cI peptide and the Nase peptide at residues 1, 2, 5, 6, 9, and 13 (see FIG. 5).

Given that the cI peptide is homologous to other I-E$^d$-restricted peptides, it was unclear why there were apparently no T-cells able to recognize it in the context of the I-E$^d$ molecule. To explain this a comparison was made of the sequences of the I-E$^d$-restricted peptides and the I-E$^d$ molecule itself. Results showed that in the third hypervariable region of the E$_\beta$chain (residues 69–81), residues 1, 2, 5. and 13 as aligned were homologous to the peptides restricted by the I-E$^d$ molecule (see FIG. 5). The cI peptide is identical to the I-E$_\beta^d$ molecule at residues 1, 2, 3, 4, 5, and 11 and homologous at 13. Furthermore, comparison of the sequences of the I-E$_\beta^d$ molecule with that of the I-E$_\beta^k$ molecule in this region, shows that residues 3, 4, 7, and 11 are the only polymorphic ones. The cI peptide is identical to the I-E$^d$ molecule at three of these polymorphic residues: the other I-E$^d$-restricted peptides are not. This identity appears to account for the presumed "hole in the repertoire."

As shown in FIG. 5, the I-E$^d$-restricted immunodominant peptide derived from influenza hemagglutinin, bears little homology to the other peptides described above (except at residues 1 and 2). This peptide however, does bear a striking homology to the I-E$_\beta^d$ molecule itself. In this case, the residues of the I-E$_\beta^d$ molecule used for comparison are taken from the second hypervariable region of the E$_\beta$chain. Mengle-Gaw, L. and H. McDevitt, *Proceeding of the National Academy of Sciences, U.S.A.*, (1983) 80:7621–7625. As aligned, residues 1, 2, 3, 4, 6, and 10 are identical and residues 7 and 9 are homologous. The influenza peptide bears an insertion with respect to the I-E$_\beta^d$ molecule at residue 5 and this residue has been shown to be an epitope for T-cell recognition. Hackett, C. et al., *Journal of Immunology*, (1985) 135:1391–1394.

SUMMARY

Thus, the work described above and in the Examples which follow shows that antigen-specific T-cell activation (i.e., activation by a specific peptide bound by a particular Class II molecule) can be inhibited by a homologous peptide if it is presented in the same Class II context as that in which the stimulatory peptide is presented. This is true even though the homologous peptide is unable to activate the T-cells. However, the same homologous peptide does not inhibit activation of T-cells which recognize the specific peptide bound by a different Class II molecule.

This supports, in the first case, competition for binding to the Class II antigen and interference by the homologous peptide in T-cell activation is the result of its binding to the Class II molecule (thus preventing the specific peptide from doing so). In the second case, it supports that because there is no competition between the homologous peptide and the specific peptide for binding to a second Class II molecule, the homologous peptide does not interfere with T-cell activation.

It has also been demonstrated that only one peptide binding site is present on each Class II molecule and that unrelated peptides restricted by a given Class II molecule act as competitive inhibitors of each other's ability to stimulate specific T-cells through competition in binding to the Class II molecule.

Comparison of the amino acid sequences of the following peptides and the I-E$^d$ Class II molecule itself supports the conclusion that selection of an immunodominant peptide within an antigen for T-cell recognition rests on its ability to bind to a transplantation antigen:

1. cI peptide, the immunodominant peptide derived from lambda repressor which is I-A$^d$ and I-E$^k$ restricted but binds most tightly to the I-E$^d$ molecule.
2. Nase peptide, the immunodominant peptide derived from Staphylococcus nuclease, which is I-A$^d$ and I-E$^d$ restricted and presumably binds to both:
3. The immunodominant peptide derived from sperm whale myoglobin, which is I-E$^d$-restricted; and
4. The immunodominant peptide derived from sperm whale hemagglutinin, which is I-E$^d$-restricted.

Comparison of peptides 1-3, summarized in the top segment of FIG. 5, showed homology among three at 6 of the 13 residues (i.e., at 1, 2, 5, 6, 9, and 13) Such homology explains their common restriction and/or ability to bind to the same Class II molecule (I-E$^d$).

Comparison of the sequences of these three I-E$^d$-restricted peptides with that of the I-E$^d$ molecule itself showed homology between four residues in the peptides and in the third hypervariable region of the I$_B$ chain. For example, in the whale myoglobin peptide, the cI peptide and the E$_\beta$chain, leucine (a non-polar amino acid) occurs at residue 1, glutamic acid at residue 2 and arginine (a basic amino acid) at residue 5: in Nase, the residue at each of these locations was the same or homologous: valine (nonpolar) at residue 1, glutamic acid (same amino acid) at residue 2 and lysine (basic) at residue 5. All three immunodominant peptides were shown to have lysine (a basic amino acid) at residue 13 and the Class II molecule to have arginine (also a basic amino acid) at that location.

Comparison of the amino acid sequences of these three peptides and the amino acid sequence of the influenza peptide, which is also I-E$^d$-restricted showed little homology. Comparison of the influenza peptide sequence with that of the second hypervariable region of the I-E$^d$ molecule showed striking homology between the two, however six residues are identical and two homologous.

The results support the conclusion that the basis of selection of an immunodominant peptide within an antigen for T-cell recognition rests upon its ability to bind to a transplantation antigen (e.g., a Class I or a Class II molecule) and that the chemical requirements for such binding rest upon a homology with a segment of the transplantation antigen itself.

These observations support the presence of internal complementary (ligand-receptor) associated with particular domains (segregated on each chain) of the Class II molecule and that the internal "ligand" for binding is, in part, encoded by the polymorphic region. The same would be expected to be true for the internal "receptor". The immunodominant peptides would then be bound to the Class II molecule, displacing the internal "ligand" and assuming equivalent geometry. Foreign "ligands" (immunodominant peptides) would then be seen by T-cells as analogs of the internal, self "ligand."

In the case of the lambda repressor peptide (cI) described above, it appears that the foreign ligand is indistinguishable (at the polymorphic sites) from the self Class II molecule and the "hole in the repertoire" is brought about by self tolerance. This idea of recognition as self, resulting in what appears to be a "hole in the repertoire," is not new. Burnet, F. M., Cambridge University Press (1959): Jerne, N., *European Journal of Immunology*, (1971) 1:1–5. However, the data presented herein provides the first molecular evidence demonstrating that the notion has a physical basis.

It is reasonable to expect that alloreactivity is a result of T-cell recognition of the internal "ligand" of a foreign Class II molecule. In the limit, if the internal "ligand" were to be composed of a number of polymorphic residues and the histotopic residues (sites of T-cell binding to the Class II molecule) were not, then a given T-cell could not distinguish between a foreign "ligand" bound to a self Class II molecule and a foreign Class II molecule bound with its own internal "ligand." If there were places of identity between the two ligands, alloreactivity would result. Given the results above (i.e., that there is homology between all "ligands"), foreign internal "ligands" could be readily considered as analogs of self and therefore chemically equivalent to self plus X. Each polymorphic residue of the foreign "ligand" would represent, in principle, a different foreign antigen in the context of self. Hence a large percentage of T-cells would be able to respond to a single allo Class II molecule. Ashwell, J. et al., *Journal of Immunology*. (1986) 136:389–395.

The sequence for the I-A$^d$-restricted, immunodominant peptide of ovalbumin (described herein) is shown in FIG. 6. It is aligned with a polymorphic region of (residues 42-55) of the A$_\beta^b$ chain. Choi, E. et al., *Science*, (1983) 221:283. It bears an identity at residues 12, 17, 19, and 20 as aligned. The single residue that is polymorphic in this region is residue 12, which is histidine in the I-A$_\beta^b$ molecule (and ovalbumin) and tyrosine in the I-A$_\beta^d$ molecule (the restricting element), as well as in the I-A$_\beta^k$ molecule. The ovalbumin-specific T-cell hybridoma, DO-11.10 which recognizes ovalbumin in the context of I-A$^d$, shows an alloreaction with I-A$_\beta^b$ but not with I-A$_\beta^k$. Furthermore, this region was shown by Germain and colleagues to control the alloreaction of DO-11.10. This histidine residue was shown by McConnell and colleagues to be essential for recognition of another ovalbuminspecific T-cell. Lechler, R. et al., *Journal of Experimental Medicine*, (1986) 163:678–696: Watts, T. et al., *Proceedings of the National Academy of Sciences, U.S.A.*, (1985) 82:5480.

This indicates that the DO-11.10 cell cannot distinguish self plus X (where X is the ovalbumin peptide) and allo (where allo is I-A$_\beta^b$).

The ovalbumin peptide described here appears to contain two regions of "permissive" residues (allowing it to bind to Class II molecules). One region involves positions 17 to 20 (T-cells like DO-11.10 require this region). The peptide deleted for these residues binds to I-A, as shown by the fact that it can stimulate T-cells like DO-54.8. Shimonkevitz, R. et al., *Journal of Immunology* (1984) 133:2167: Watts, T., et al., *Proceedings of the National Academy of Sciences, U.S.A.*, (1985) 82:5480. Recent evidence indicates that residues in the region preceding position 12 also form a "permissive" framework for I-A$^d$ binding. Cease, K. B. et al., *Journal of Experimental Medicine*, (1986) 164:1779. T-cells recognizing a peptide derived from sperm whale myoglobin in the context of I-A$^d$ also show an alloreaction with I-A$^b$. Berkower, I. et al., *Journal of Immunology*, (1986)

164:1779. Myoglobin shows a homology with the 1-A$^b$ molecule at positions 2, 5, 7, 8, and 12 (FIG. 6). Here, too, it appears that the histidine residue at position 12 is responsible for the similarity between myoglobin in the context of self, I-A$^d$, and allo, I-A$^b$.

An obvious homology motif may not always be found among peptides restricted by the same Class II molecule. Motifs associated with each ligand-like domain will be found (FIGS. 5 and 6). FIG. 7 presents a compilation of the data which indicates that there are three motifs associated with ligands for the I-A$^d$ molecule. The alignments in FIG. 8 indicate the possibility of two motifs for the I-E$^k$ molecule.

EXAMPLE I

Preparation of T-cell Hybridomas and Antigen-Presenting Cells

The I-A$^d$-I-E$^k$ positive A20.2J Balb/c B lymphoma line which presents antigen in an MHC restricted fashion to T-cells was a gift from Drs. J. Kappler and P. Marrack. DO-11.10 is an ovalbumin I-A$^d$ restricted T-cell hybridoma. Shimonkevitz, R. et al., *Journal of Immunology*, (1984) 133:2067–2074. TA.3 is an antigen-presenting cell line obtained by fusing lipopolysaccharide stimulated B-cells from (Balb/c x A/J)F1 donors with cells from the M12.4.1 Balb/c B lymphoma cell line (a gift from Dr. L. Glimcher). The phenotype of TA3 B-cell-B lymphoma hybridomas, I-A$^{k/d}$I-E$^{k/d}$, make this cell line able to present antigen to either H2$^d$ or H2$^k$ restricted T$_h$ (T-helper lymphocytes) cell hybridomas.

Culture Conditions. T-cell hybridomas as well as antigen presenting cells were maintained in large wells (24 well plates, Costar no. 3424) in RPMI 1640 medium supplemented with $2 \times 10^{-3}$ M glutamine, $5 \times 10^{-5}$ M 2-mercaptoethanol, 100 $\mu$/ml penicillin, 100 $\mu$g/ml streptomycin and 10% fetal bovine serum (Grand Island Biological Company, no. 200.6140). The cell lines were duplicated every two days by serial dilution and expanded in T25 and T75 flasks (Falcon) with, respectively, 5 ml and 50 ml of medium before they were used in the work described below.

Peptides. All peptides were synthesized by the solid phase method of Merrifield as previously described. Merrifield, R., *Journal of the American Chemical Society*, (1963) 85:2149–2154. The amino acid composition and the sequence analysis of the synthesized peptides correspond to the expected compositions. The purity of the peptides as determined by sequence and/or HPLC is 93–94%.

EXAMPLE II

Inhibition of Antigen-Specific T-cell Activation by Non-Stimulatory Peptide Analogs The T-cell hybridoma 7B7.3 was derived from a Balb/c mouse immunized with lambda repressor. It can be stimulated with the peptide P15–26 (residues 15–26 of the immunogen) in the context of I-A$^d$. The T-cell hybridoma 8I, derived from the A/J strain, recognizes the same peptide but in the context of I-E$^k$. Neither T-cell can be stimulated with a homologous peptide analog P12–24 (residues 12–24 of the immunogen). Other T-cells, however, derived from Balb/c can recognize P12–24 in the context of I-A$^d$.

This suggests that P12–24 can bind to the I-A$^d$ molecule but presumably cannot stimulate 7B7.3 because it lacks a specific T-cell interaction residue (epitopes). The activation of T-cell hybridomas was measured by their ability to secrete IL-2 (T-cell hybridomas ($5 \times 10^4$) that were incubated with $5 \times 10^4$ antigen-presenting cells in wells of a 96-well tissue Costar plate (no. 3596) in 200 $\mu$l RPMI complete medium containing the appropriate antigen concentrations). After 24 hrs of culture, supernatant (50 $\mu$l) was removed and then assayed for IL-2 content by its ability to maintain the growth of the IL-2 Dependent CTL-L cells: 1 $\mu$Ci of $^3$H tritiated thymidine was added per well. Six hours later the cells were harvested by an automatic cell harvester (Skartron Inc., Sterling, Va.) and thymidine incorporation measured by scintillation counting.

Since both peptides share 11 of 13 residues, inhibition of P15–26-dependent 7B7.3 activation was observed when the peptide P12–24 was also included in the cultures. See FIG. 2.

Figure 2:
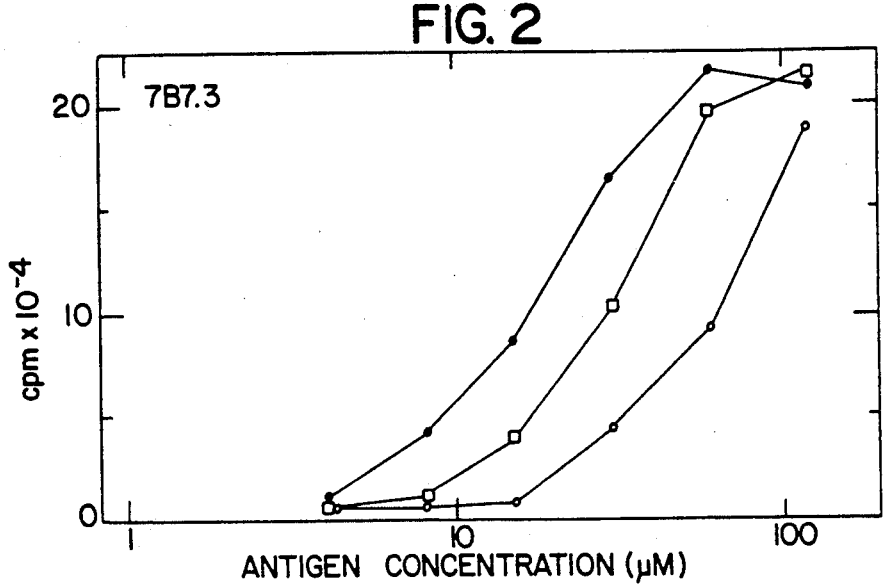
FIG. 2 is a graphic representation of the inhibition of activity of T-cell hybridoma 7B7.3 by related peptides. Activity was measured in the presence of various concentrations of P15-26, in medium (RPMI 1640) alone (•-•) or in the presence of P12-24 at 20 μM (◐-◐) or at 60 μm (○-○). A20 B-cell lymphoma (5×10⁴ cells/well) was used as antigen-presenting cells. After 24 hours of culture, 50 μl supernatant were harvested and assayed for IL-2 concentration by following incorporation of [³H] thymidine into the IL-2 dependent CTL-1 cell line 10⁴ cells/well). The values represent the arithmetic mean of triplicate samples taken from the experiments carried out ab initio.

The activity of T-cell hybridoma 7B7.3 was measured in the presence of various concentrations of P15–26, either in RPMI 1640 with 10 percent fetal calf serum alone or in the presence of P12–24 20 $\mu$M or P12–24 60 $\mu$M. A20 B-cell lymphomas ($5 \times 10^4$ cells/well) were used as antigen presenting cells. After 24 hrs of culture, supernatant (50 $\mu$l) was harvested and then assayed for IL-2 concentration by following incorporation of $^3$H thymidine into the IL-2 dependent CTL-L cell line ($10^4$ cells/well). The indicated values in FIG. 2 represent the arithmetic mean of triplicate samples.

Figure 3:
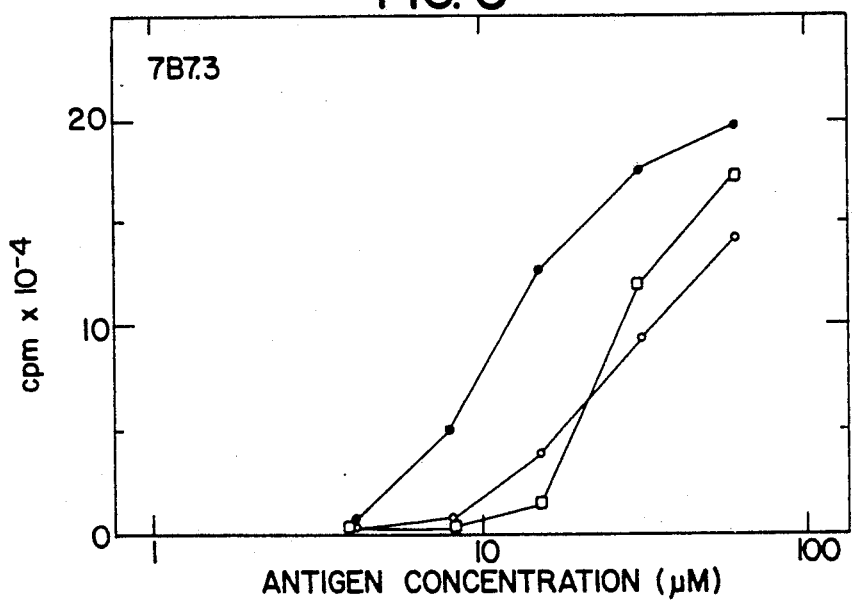
FIG. 3 is a graphic representation of the inhibition of activity of T-cell hybridoma 7B7.3 by chicken ovalbumin (Ova) or *Staphylococcal nuclease* (Nase). Activity was measured in the presence of various concentrations of P15-26, in (RPMI 1640) medium alone (•-•) or in the presence of 30 μM of Ova (P324-336) (◐-◐) or 60 μM of Nase (P61-80) ( ). The values represent the arithmetic means of triplicate values as explained in FIG. 2.

In the case of 7B7.3, P12–24 was found to inhibit activation by P15–26 in a dose dependent manner. The potency of the inhibition depends on the inhibitor concentration. As shown in FIG. 3, P12–24 changed the apparent affinity of P15–26 to 7B7.3; the 50% stimulation point of the P15–26 antigen dose response curve is at a concentration of 20.7±1.2 $\mu$M when P15–26 is cultured with 7B7.3 alone. When 7B7.3 is co-cultured with P15–26 and P12–24, the 50 percent stimulation point is 29.8±2.8 $\mu$M and 70.3 $\mu$M when P12–24 is at 20 $\mu$M and 60 $\mu$M, respectively. The inhibitory effect can be reversed by increasing the concentration of P15–26 in culture. The sample peptide, P12–24, had no effect on the IL-2 response of hybridoma 8I, a P12–26 responsive, I-E$^k$-restricted T-cell hybridoma. It has also been demonstrated that the residues of P12–26 required for interaction with I-A$^d$ and I-E$^k$ are different. The absence of inhibition of the I-E$^k$-restricted T-cells by P12–24 may therefore be due to the inability of that peptide to bind to the I-E$^k$ molecules.

EXAMPLE III

Inhibition of Repressor-Specific T-cell Activation by Other I-A$^d$-Restricted Peptides The following work was carried out to examine the competitive ability of peptides derived from Staphylococcus nuclease (Nase), residues 61–80 (P61–80) and from ovalbumin (Ova), residues 324–336 (P324-336) to inhibit P15–26-dependent activation of the hybridoma 7B7.3. Each of these peptides has been shown in their respective cases to be I-A$^d$-restricted and to be immunodominant for their respective antigens. Finnegan, A. et al. *Journal of Experimental Medicine* (1986) 164:897-910: Shimonkevitz, R. et al., *Journal of Immunology* (1984). $5 \times 10^4$ TA3 cells were added to each well. Various concentrations of P15–26 were added with either medium (RPMI 1640 with 10 percent fetal calf serum) alone or 30 $\mu$M or Ova (P324-36) of 60 $\mu$M of Nase (P62–80). A20 B-cell lymphoma ($5 \times 10^4$ cells/- well) was used as antigen presenting cells. 7B7.3 T-cell hybridomas (5×10⁴) were then added and cultured for 24 hrs. The level of T-cell stimulation was assayed by determining the IL-2 concentration as indicated in Example II. As shown in FIG. 3, these peptides inhibit 7B7.3 activation in a dose-dependent manner. The degree of inhibition is independent upon the ratio of activator to inhibitor in each case.

8I (I-E$^k$-restricted) T-cell hybridomas and TA3 B presenting cells (5×10⁴) were cocultured with various concentration of P15-26 and either medium alone or 60 $\mu$M of Ova (P324-336) or 60 $\mu$M Nase (P61-80) as described above. Specificity is seen in that the same peptides are without effect on the I-E$^k$-restricted-P15-26-specific T-cell, 8I. In addition, no other peptides representative of the remainder of the Nase sequence were able to inhibit 7B7.3 activation.

EXAMPLE IV

Inhibition of Ovalbumin-Specific T-cell Activation by Other I-A$^d$-Restricted Peptides The T-cell hybridoma DO-11.10 is ovalbumin-specific, and I-A$^d$-restricted. It responds to the peptide P323-339 derived from ovalbumin. It responds less well to the truncated analog P324-336, which was used as a stimulator. As inhibitors, the lambda repressor peptide P12-26 and a peptide influenza hemagglutinin site 2 (P126-138) derived from influenza hemagglutinin (I-A$^d$-restricted) were used. Neither of these peptides can stimulate DO-11.10 on its own. DO-11.10 was cultured with various concentrations of Ova (P324-336) and A20 presenting cells, either in medium alone or in the presence of influenza hemagglutinin P111-120 or P12-26 or influenza hemagglutinin site 2 (P126-138), each at 50 $\mu$M. After 24 hrs of culture, stimulation was determined by quantitating the amount of IL-2 released. In FIG. 4, the values represent the arthmetic mean of triplicate samples. Conditions were as described in Example III.

As shown in FIG. 4, these non-stimulatory peptides act as inhibitors for ovalbumin-specific T-cell activation. The influenza hemagglutinin-derived peptide P111-120, which is I-E$^d$-restricted, served as a control; it had no effect on ovalbumin-specific T-cell activation.

EXAMPLE V

Binding of Repressor Peptide P12-26 to Class II Molecules In Vitro

To gain further insight into the mechanism of competitive inhibition observed between peptides restricted by the same Class II molecule, a study of peptide binding to Class II molecules in vitro was conducted. Results are shown in Table 1.

The peptide P12-26 was modified by the addition of a tyrosine residue to the N-terminus to serve as an acceptor for the $^{125}$I.

Ia-molecules were purifed from Nonidet P-40 (NP-40) lysates of A20 (H2$^d$) or AKTB-1b (H2$^k$) cells by affinity chromatography using the following monoclonal antibodies: MK-D6 (I-A$^d$-specific), 10-3-6 (I-A$^k$-specific) specific) or 14-4-4 (I-E$^{d/k}$-specific) coupled to Sepharose 4B beads (Pharmacia Fine Chemicals, Sweden).

A gel filtration assay was used for determining the degree of association between immunogenic peptides and Ia. The assay is described in: Buus, S. et al., *Proceeding of the National Academy of Sciences, U.S.A.* (1986) 83:3968, the teaching of which is incorporated herein by reference. Briefly, 40 $\mu$mole of purified Ia in 1 percent NP-40/PBS was mixed with 0.2 $\mu$mole of $^{125}$I-labeled peptide (approximately 200,000 cpm for each experiment) and incubated for 48 hours at room temperature to allow for formation of the Ia-peptide complex. The Ia-peptide complexes were separated from free peptide by gel filtration and the percentage of peptide bound to Ia was calculated as the ratio of the $^{125}$I-labeled peptide in the void volume to the total $^{125}$I-labeled peptide recovered.

TABLE 1

| Binding of $^{125}$I cI P12-26 Analog to Class II Molecules | |
|---|---|
| Class II Antigen | Percent of Peptide Bound |
| I-A$^d$ | 1.6 ± 0.8 (n = 5) |
| I-E$^d$ | 8.9 ± 2.2 (n = 7)* |
| I-A$^k$ | 0.3 ± 0.5 (n = 5) |
| I-E$^k$ | 2.3 ± 1.7 (n = 5) |

*Level of binding is significantly different from the other Class II molecules at the greater than 99 percent confidence level.

As shown in Table 1, the peptide P12-26 is able to bind to both molecules as expected. (The modified form of P12-26 used for binding is as active for T-cell activation as P12-26.) Specificity is apparently shown by the inability of P12-26 to bind to the I-A$^k$ molecule: the latter does not show acitivity in vivo for restriction of this peptide. The peptide P12-26, however, binds exceedingly well to the I-E$^d$ molecule. No T-cells from Balb/c immune mice were found to be restricted by this molecule.

To determine if the binding of P12-26 is nonspecific for the I-E$^d$ molecule, examination was carried out of its ability to compete for binding with a myoglobin derived peptide, shown to be restricted by (and to bind to) I-E$^d$. Results are shown in Table 2.

For the inhibition assay a dose-range of unlabeled cI P12-26 peptide was added to the incubation mixture of Ia and $^{125}$I-labeled peptide (600, 120, 24, ad 48 $\mu$M). The degree of association between Ia and labeled peptide was determined by gel filtration as described in Table 1. The percentage of peptide bound in the absence of inhibitors is 10.6 percent for ovalbumin (323 to 339)/I-A$^d$; 6.5 percent for myoglobulin 132 to 153)/I-E$^d$; 21.5 percent for lysozyme (46 to 61)/I-A$^k$; 2.5 percent for cytochrome C (88 to 104)/I-E$^k$. The concentration of inhibitory peptide required to obtain a 50 percent inhibition of binding was calculated. Each experiment was repeated three times.

TABLE 2

Capacity of Lambda-Repressor Peptide P12-26 to Inhibit Binding of Isotopically Labeled Peptides to Various Class II Antigens

| $^{125}$I Labeled Peptide | Class II Molecule Bound | Concentration ($\mu$M) of P12-26 Required for 50 percent Inhibition |
|---|---|---|
| Ovalbumin (P323-339)* | I-A$^d$ | 300 |
| Myoglobin (P132-153) | I-E$^d$ | 4 |
| Lysozyme (Hen) (P46-61) | I-A$^k$ | greater than 2,500+ |
| Cytochrome c (pigeon) (P88-104) | I-E$^k$ | 300 |

*Numbers in parenthesis refer to the amino acid residue positions in the parent molecule.
+No inhibition of binding was detected at 2500 $\mu$M of P12-26.

P12-26 also competes with other immunodominant peptides for binding to their respective Class II molecules. Competition, however, is not observed for the lysozyme-derived peptide, restricted by I-A$^k$, a Class II molecule not bound by P12-26 (see Table 1). It is noteworthy that in fact, P12-26 binds best to the I-E$^d$ molecule, as shown by its relative binding ability and its relative competitive ability.

In view of the result, indicating that P12-26 binds specifically to the I-E$^d$ molecule, the question as to whether or not there were T-cells restricted by I-E$^d$ in the Balb/c mouse immunized with the NH$_2$-terminal domain of cI was re-examined.

Of more than 300 hybrids specific for P12-26 recovered from 15 cI immune mice, none were shown to be restricted by the I-E$^d$ molecule. That is, they could be stimulated by antigen in the presence of L cells expressing I-A$^d$, but could not be shown to be stimulated by antigen in the presence of L cells expressing I-E$^d$.

In contrast, of 80 hybrids specific for myoglobin (P135-147), 78 were shown to be restricted to I-E$^d$ as assayed on L cells expressing I-E$^d$. Furthermore, unfractionated lymph node-derived T-cells from P12-26 immune mice showed significant proliferation (68,000 cpm thymidine incorporation) when cultured in a standard lymph node proliferation assay as described by Shastri et al. with 10 $\mu$M P12-26 (Shastri et al., *Journal of Experimental Medicine*, (1986) 164:882). However, the lymph node cells failed to show significant proliferation (1250 cpm) above cultures with no antigen added when the monoclonal antibody, MKD6, specific for the I-A$^d$ molecule, was added to identical cultures with 10 $\mu$M P12-26. The proliferation of these same cultures was not inhibited (75,000 cpm) by a monoclonal antibody, 34-1-4S, which is specific for I-E$^d$ and which inhibits the stimulation of a hemocyanin specific, I-E$^d$ resticted T-cell hybridoma.

Thus, there appears to be an absence of T-cells in cI immune mice able to recognize P12-26 in the context of the I-E$^d$ molecule: there is apparently a hole in the repertoire with respect to P12-26 and the I-E$^d$ molecule.

The next study was involved with a synthetic polypeptide for use as a malaria vaccine.

MATERIALS

The synthesis and analysis of synthetic peptides has been described previously (Guillet et al., supra). Peptides used in this study were:

P12-26, derived from the cI protein of bacteriophage lambda.

P12-26 LF is a variant of P12-26 in which residues 14 and 15 are replaced by LF.

(NANP)1-12-26, (NANP)2-12-26, and (NANP)3-12-26 are respectively 19, 23, and 27 residues long. They begin with NANP repeated 1-3 times followed by P12-26.

NANP-50 is a polymer of NANP repeated 50 times.

METHODS

Antibody Production

For antibody production, mice were given a primary intraperitoneal and foot pad injection of 100 $\mu$g of antigen (NANP)3-12-26) emulsified in complete Freund's Adjuvant (CFA) on day 0 followed by a secondary subcutaneous injection of 50 $\mu$g of antigen on day 21 with incomplete Freund's Adjuvant (IFA). Sera from a bleed on days 7, 21 (before boost) 28, and 42 were used.

T-cell Proliferation

For T-cell proliferation studies 100 $\mu$g of (NANP)3-12-26 emulsified in CFA was injected in the base of the tail and also food pad of mice on day 0. On day 10, draining nodes were removed. Cells were seeded at $8 \times 10^5$/well flat bottom microtiter plates $\frac{1}{2}$ volume in 0.1 ml RPMI containing 10% FCS, $5 \times 10^5$ M2ME, penicillin, streptomycin and antigen. On day 2, 1 $\mu$Ci of $^3$H thymidine (ICN) was added to triplicate or duplicate cultures. 16 hr later cells were harvested and incorporated $^3$H was assayed by scintillation counter.

Estimation of Antibody Titer Against NANP3 (NANP)$_n$, where n indicates number of repeats)

An ELISA test was used. NANP50 or 12-26-BSA conjugated (10 $\mu$g/ml, 2 $\mu$g/ml, respectively (25 $\mu$l )) was added to polyvinyl wells for 1 hr at room temperature or overnight at 4° C. Wells were then blocked, sera added and a goat anti-mouse IgG coupled to peroxidase was added (1$\times$1000 dilution). Finally, substrate (ABTS) was added and absorbance was read at 405 nm. Sera were tested at various dilutions.

RESULTS

(NANP)3-12-26 Stimulates T-cells Specific for P12-26

Activation of T-cell hybridoma 9H35 and 9C127 was studied. Antigen presenting cells were the B-cell lymphoma A20 and the antigen, either P12-26 or (NANP)3-12-26, was added at various doses (0-50 $\mu$g/ml). IL-2 release was taken as a measure of activation of T-cells and was assayed on an indicator cell line requiring IL-2 for growth.

The results obtained showed that for two H2$^d$-restricted T-helper cell hybridomas, 9H35 and 9C127, specific for P12-26 (isolated from cI protein-immunized animals), the peptide (NANP)3-12-26 is able to act as a stimulator in the presence of suitable (A20) antigen presenting cells. The NANP-containing peptide is more active. This result demonstrates that the T-cell stimulatory capacity of an extended Class II-binding peptide is not greatly altered as studied in vitro.

The (NANP)-3-12-26 Peptide can be Bound by Both Monoclonal Antibodies Specific for (NANP)50, and One Specific for P12-26

Antibody recognition of (NANP)3-12-26 by monoclonal antibodies was studied. The antigen, bovine serum albumin (BSA) conjugated to P12-26 was adsorbed to microwells and horseradish peroxidase (HRP) labeled antibody specific for P12-26 added. In the absence of (NANP)3-12-26 or in the presence of P12-26LF, there is no inhibition of monoclonal antibody B3.11 binding. Inhibition is observed with P12-26, (NANP)3-12-26, and P12-26S (position 18), in the order of decreasing inhibition.

The above study was repeated except the antigen was radiolabelled (NANP)$_{50}$ which was bound to microwells. It was found that P12-26 or (NANP)2-12-26 did not inhibit binding while (NANP)3 and (NANP)3-12-26 did inhibit binding.

The results demonstrate that the monoclonal antibody, B3.11 can be inhibited in its binding to bovine serum albumin coupled with P12-26 by the addition of (NANP)3-12-26. Similarly, a monoclonal antibody specific for (NANP)$_{50}$, isolated from malarial parasite-immune mice, can be inhibited in its binding by the (NANP)3-12-26 peptide. These results again demonstrate that antibodies specific for the NANP portion of the synthetic molecule are able to recognize the "hapten" in the presence of an additional Class II-binding peptide.

Mice Unable to Synthesize Antibodies to (NANP)$_{50}$ when (NANP)$_{50}$ or (NANP)3 are Used for Immunization, are able to Synthesize Antibodies to (NANP)$_{50}$, (NANP)3, and to Sporozoites when (NANP)3-12-26 is used as an Immunogen Pairs of mice were immunized with (NANP)3-12-26, (NANP)$_{50}$, (NANP)1-12-26, and (NANP)2-12-26. The serum titers were tested by direct binding assays as indicated in the methods section at either seven days after a primary immunization, 20 days after, or ten days after a secondary boost (control sera gave no detectable binding). Sera from mice immunized with (NANP)3-12-26 (10 days after secondary boost) were found to bind directly to circumsporozoite falciparum by conventional radiolabelled anti-mouse globulin RIA.

Lymph node-derived T-cell proliferation was observed in mice eight days after immunization with (NANP)3-12-26. T-cell proliferation as assayed by thymidine incorporation was seen with the immunogen, P12-26, (NANP)1-12-26, and (NANP)2-12-26. No proliferation is seen with (NANP)3 or (NANP)$_{50}$ in these same mice. These results indicate that the presence of Class II molecule binding sequences on the immunogen are sufficient to impart T-cell stimulatory activity to (NANP)3 which on its own is inactive in these mice. All T-cell activity is directed to the Class II binding sequence. These results support that the antibody activity can be induced in mice immunized with (NANP)3-12-26 against the (NANP) sequences present on the 12-26 portion of the immunogen, and that such an "activating" sequence can be added to inactive sequences and generate antibodies against the latter.

In a similar experiment, Balb/c mice immunized with (NANP)3-12-26LF showed T-cell proliferative responses (taken from the spleen 16 days post immunization) to the immunogen but not to (NANP)3-12-26 (no more than to P12-26 alone). This result again shows that there is no induction of T-cell reactivity to the (NANP) portion of the immunogen. In this case, as described in the paragraph above, it is clear that (NANP)3-12-26 can bind to Class II molecules and present to T-cells for activation. Mice immunized with the (NANP)3-12-26LF also induce antibodies specific for the (NANP)$_{50}$ polymer. These antibodies are of the $\mu$ and $\gamma$-1 class.

The inability to detect T-cell reactivity to the (NANP) portion of the immunogen is a property of Balb/c mice and not the property of the immunogen. 57B6/H-2b mice which were immunized with (NANP)3-12-26, are able to respond directly to (NANP)3 or (NANP)$_{50}$, and respond to immunization with (NANP)3-12-26 with T-cell reactivity to the (NANP) portion of the immunogen.

Thus, the utility of this method is shown in a system which has utility for the production of immunity to a human pathogen.

The above results demonstrate the power and breadth of the subject invention in modulating the immune system in a wide variety of contexts, both in vitro and in vivo, both as to stimulating B- and/or T-cells or inactivating B- and/or T-cells. The subject invention provides for exquisite specificity in selecting for one or more subsets of lymphocytes in response to a particular event and, furthermore, in relation to the context of the host, that is, the transplantation antigens of the host. By virtue of the ability to mimic a polymorphic region of the transplantation antigens of a particular host, the T-cell immune system may be substantially inactivated. By contrast, by varying the consensus sequence for binding to the transplantation antigens of the target host(s) one can activate specifically one or a few subsets of lymphocytes to provide for a stimulated immune system for purposes of vaccination, enhanced response to a pathogenic invader, or other event associated with protection by the immune system. In addition, one can modulate the autoimmune system by inactivating lymphocytes associated with attack on native tissue. Thus, there is an extensive spectrum of uses of the subject invention for enhancing or diminishing particular cells in relation to their function.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for modulating the immune response of a cellular system to an epitope of a first antigen to which said cellular system is immunologically responsive, said cellular system comprising T-cells restricted by a first Class II transplantation antigen and antigen presenting cells comprising said first Class II transplantation antigen, said method comprising:

bringing together said cellular system with a polypeptide of fewer than about 100 amino acids consisting essentially of: a first domain of an about 8 to 30 amino acid sequence of an immunodominant sequence containing an agretope and said epitope of said first antigen or a mutated sequence thereof restricted by said transplantation antigen; and a second domain comprising an epitopic site of a second antigen other than said first antigen, wherein said polypeptide has a higher binding affinity site for said transplantation antigen than said second antigen, as a result of the presence of said immunodominant sequence or mutated sequence thereof;

whereby the immune response of said cellular system to said epitope of said first antigen is modulated.

2. A method according to claim 1, wherein said polypeptide is of fewer than about 75 amino acids.

3. A method according to claim 1, wherein said cellular system is whole blood.

4. A method according to claim 1, wherein said second antigen is the antigen of a pathogen.

5. A method according to claim 4, wherein said pathogen is a virus.

6. A method according to claim 4, wherein said pathogen is a parasitic organism.

7. A method according to claim 4, wherein said pathogen is a bacterium.

8. A method for modulating the immune response of a cellular system to an epitope of a first antigen to which said cellular system is immunologically responsive, said cellular system comprising T-cells restricted by a first Class II transplantation antigen and antigen presenting cells comprising said first Class II transplantation antigen, said method comprising:

bringing together said cellular system with a polypeptide of fewer than about 75 amino acids consisting essentially of: a first domain of an about 8 to 30 amino acid sequence of an immunodominant sequence of a naturally occurring first antigen containing an agretope and said epitope of said first antigen and restricted by said transplantation antigen; and a second domain comprising an epitopic site of a second antigen, wherein said polypeptide has a higher binding affinity site for said transplantation antigen than said second antigen;

whereby the immune response of said cellular system to said epitope of said first antigen is modulated.

9. A method according to claim 8, wherein said cellular system is whole blood.

10. A method according to claim 9, wherein said first antigen is the antigen of a virus.

11. A method according to claim 9, wherein said second antigen is the antigen of a pathogen.

12. A method for modulating the immune response of a cellular system to an epitope of a first antigen to which said cellular system is immunologically responsive, said cellular system comprising T-cells restricted by a first Class II transplantation antigen and antigen presenting cells comprising said first Class II transplantation antigen, said method comprising:

bringing together said cellular system with a polypeptide of fewer than about 75 amino acids consisting essentially of: a first domain of an about 8 to 30 amino acid sequence of an immunodominant mutated sequence containing an agretope and said epitope of said first antigen and restricted by transplantation antigen, whereby said mutation results in greater conformity with the consensus sequence of the agretope restricted by said transplantation antigen; and a second domain comprising an epitopic site of a second antigen other than said first antigen;

whereby said immune response of said cellular system to said epitope of said first antigen is modulated.

13. A method according to claim 12, wherein said cellular system is whole blood.

* * * * *